United States Patent
Matsunuma et al.

(10) Patent No.: US 11,457,201 B2
(45) Date of Patent: Sep. 27, 2022

(54) IMAGING DEVICE AND ELECTRONIC APPARATUS

(71) Applicant: SONY SEMICONDUCTOR SOLUTIONS CORPORATION, Kanagawa (JP)

(72) Inventors: Takeshi Matsunuma, Kanagawa (JP); Motonari Honda, Kanagawa (JP)

(73) Assignee: SONY SEMICONDUCTOR SOLUTIONS CORPORATION, Kanagawa (JM)

( * ) Notice: Subject to any disclaimer, the term of this patent is extended or adjusted under 35 U.S.C. 154(b) by 0 days.

(21) Appl. No.: 17/293,733

(22) PCT Filed: Feb. 27, 2019

(86) PCT No.: PCT/JP2019/007601
§ 371 (c)(1),
(2) Date: May 13, 2021

(87) PCT Pub. No.: WO2020/105201
PCT Pub. Date: May 28, 2020

(65) Prior Publication Data
US 2022/0007001 A1  Jan. 6, 2022

(30) Foreign Application Priority Data
Nov. 22, 2018  (JP) ............................. JP2018-219411

(51) Int. Cl.
*H04N 13/204* (2018.01)
*H04N 13/106* (2018.01)
(Continued)

(52) U.S. Cl.
CPC ......... *H04N 13/204* (2018.05); *H04N 5/2254* (2013.01); *H04N 13/106* (2018.05);
(Continued)

(58) Field of Classification Search
CPC ... H04N 13/204; H04N 13/106; H04N 5/2254
See application file for complete search history.

(56) References Cited

U.S. PATENT DOCUMENTS

| 2010/0289878 | A1* | 11/2010 | Sato ..................... H04N 13/239 348/46 |
| 2013/0016189 | A1* | 1/2013 | Hosaka ................ H04N 13/239 348/E13.074 |

(Continued)

FOREIGN PATENT DOCUMENTS

| CN | 105814401 A | 7/2016 |
| CN | 108738372 A | 11/2018 |

(Continued)

OTHER PUBLICATIONS

International Search Report and Written Opinion of PCT Application No. PCT/JP2019/007601, dated May 7, 2019, 09 pages of ISRWO.

*Primary Examiner* — Rowina J Cattungal
(74) *Attorney, Agent, or Firm* — Chip Law Group

(57) ABSTRACT

An imaging device capable of further increasing the accuracy of distance information and an electronic apparatus equipped with the imaging device are provided. The present technology provides an imaging device that includes a stereo imager, and the stereo imager includes a plurality of sensors. Each sensor of the plurality of sensors has an imaging unit formed with a plurality of repeating units. The imaging unit includes a polarizer having at least one kind of polarization spindle angle, and at least two unit images obtained by a plurality of the imaging units are combined, to obtain information about polarization in at least three directions, and generate normal information. The present technology further provides an electronic apparatus equipped with the imaging device.

17 Claims, 27 Drawing Sheets

(51) Int. Cl.
    *H04N 5/225*     (2006.01)
    *A61B 1/05*      (2006.01)
    *B60R 11/04*     (2006.01)

(52) U.S. Cl.
    CPC ............... *A61B 1/05* (2013.01); *B60R 11/04* (2013.01); *B60R 2300/107* (2013.01)

(56) References Cited

U.S. PATENT DOCUMENTS

| | | | |
|---|---|---|---|
| 2013/0033575 A1* | 2/2013 | Kobayashi | H04N 13/296 |
| | | | 348/46 |
| 2014/0092227 A1 | 4/2014 | Kanamori et al. | |
| 2016/0261852 A1 | 9/2016 | Hirasawa | |
| 2018/0075615 A1* | 3/2018 | Myokan | H04N 9/045 |
| 2020/0183066 A1* | 6/2020 | Mitani | G03B 17/00 |
| 2020/0185436 A1* | 6/2020 | Mitani | H04N 5/238 |
| 2021/0165144 A1* | 6/2021 | Yamazaki | G01N 21/21 |

FOREIGN PATENT DOCUMENTS

| | | |
|---|---|---|
| EP | 3086085 A1 | 10/2016 |
| JP | 2009-162847 A | 7/2009 |
| JP | 2015-114307 A | 6/2015 |
| KR | 10-2018-0108592 A | 10/2018 |
| WO | 2009/147814 A1 | 12/2009 |
| WO | 2013/175686 A1 | 11/2013 |
| WO | 2015/093205 A1 | 6/2015 |
| WO | 2018/074064 A1 | 4/2018 |
| WO | 2018/142692 A1 | 8/2018 |

\* cited by examiner

IMAGING DEVICE AND ELECTRONIC APPARATUS

CROSS REFERENCE TO RELATED APPLICATIONS

This application is a U.S. National Phase of International Patent Application No. PCT/JP2019/007601 filed on Feb. 27, 2019, which claims priority benefit of Japanese Patent Application No. JP 2018-219411 filed in the Japan Patent Office on Nov. 22, 2018. Each of the above-referenced applications is hereby incorporated herein by reference in its entirety.

TECHNICAL FIELD

The present technology relates to imaging devices and electronic apparatuses.

BACKGROUND ART

There have been suggested techniques relating to an image processing device that generates information about the normal on the surface of an object by capturing images of the object (see Patent Document 1, for example).

CITATION LIST

Patent Document

Patent Document 1: WO 2009/147814 A

SUMMARY OF THE INVENTION

Problems to be Solved by the Invention

However, there is a possibility that the technique suggested in Patent Document 1 is unable to further increase the accuracy of distance information.

Therefore, the present technology has been made in view of such circumstances, and the principal object thereof is to provide an imaging device capable of further increasing the accuracy of distance information, and an electronic apparatus equipped with the imaging device.

Solutions to Problems

As a result of intensive studies conducted to achieve the above object, the present inventors have succeeded in further increasing the accuracy of distance information, and have completed the present technology.

Specifically, a first aspect of the present technology provides an imaging device including
a stereo imager, in which
the stereo imager includes a plurality of sensors,
each sensor of the plurality of sensors has an imaging unit formed with a plurality of repeating units,
the imaging unit includes a polarizer having at least one kind of polarization spindle angle, and
at least two unit images obtained by a plurality of imaging units are combined, to obtain information about polarization in at least three directions, and generate normal information.

In the imaging device of the first aspect according to the present technology, a polarizer having the at least one kind of polarization spindle angle included in one imaging unit of the plurality of imaging units, and a polarizer having the at least one kind of polarization spindle angle included in each of the plurality of imaging units other than the one imaging unit may differ from each other in the polarization spindle angle, and each of the imaging units other than the one imaging unit may not include the polarizer having the at least one kind of polarization spindle angle included in the one imaging unit.

In the imaging device of the first aspect according to the present technology, a plurality of the unit images may be reconstructed on the basis of a stereo correspondence relationship.

In the imaging device of the first aspect according to the present technology, each imaging unit of the plurality of imaging units may include a polarizer having two or less kinds of the polarization spindle angles.

In the imaging device of the first aspect according to the present technology, each imaging unit of the plurality of imaging units may include a polarizer having two kinds of the polarization spindle angles, and the two kinds of the polarization spindle angles may be orthogonal to each other in each imaging unit of the plurality of imaging units.

In the imaging device of the first aspect according to the present technology, one imaging unit of the plurality of imaging units may include a polarizer having a polarization spindle angle of 22.5 degrees and a polarizer having a polarization spindle angle of 112.5 degrees, and another imaging unit of the plurality of imaging units may include a polarizer having a polarization spindle angle of 67.5 degrees and a polarizer having a polarization spindle angle of 157.5 degrees.

In the imaging device of the first aspect according to the present technology, each imaging unit of the plurality of imaging units may include a polarizer having one kind of polarization spindle angle, and the difference in the polarization spindle angle among the polarizers of the respective imaging units of the plurality of imaging units may be not smaller than five degrees and not greater than 85 degrees.

In the imaging device of the first aspect according to the present technology, each imaging unit of the plurality of imaging units may have repeating units including a polarizer and repeating units not including a polarizer, and the ratio between the repeating units including a polarizer and the repeating units not including a polarizer may be substantially the same among the respective imaging units of the plurality of imaging units.

In the imaging device of the first aspect according to the present technology, each imaging unit of the plurality of imaging units may have repeating units including a polarizer and repeating units not including a polarizer, and the layout pattern of the repeating units including a polarizer and the repeating units not including a polarizer may be substantially the same among the respective imaging units of the plurality of imaging units.

Further, a second aspect of the present technology provides an imaging device including
a stereo imager, in which
the stereo imager includes a first sensor and a second sensor,
the first sensor has a first imaging unit formed with a plurality of repeating units,
the second sensor has a second imaging unit formed with a plurality of repeating units,
the first imaging unit includes a polarizer having at least one kind of polarization spindle angle, the second imaging unit includes a polarizer having at least one kind of polarization spindle angle, a first unit image obtained by the first imaging unit and a second unit image obtained by the second imaging unit are combined, to acquire information about polarization in at least three directions, and generate normal information.

In the imaging device of the second aspect according to the present technology, the polarizer of the first imaging unit having at least one kind of polarization spindle angle, and the polarizer of the second imaging unit having at least one kind of polarization spindle angle may differ from each other in the polarization spindle angle, and the second imaging unit may not include the polarizer of the first imaging unit having at least one kind of polarization spindle angle.

In the imaging device of the second aspect according to the present technology, the first unit image and the second unit image may be reconstructed on the basis of a stereo correspondence relationship.

In the imaging device of the second aspect according to the present technology, the first imaging unit may include a polarizer having two or less kinds of polarization spindle angles, and the second imaging unit may include a polarizer having two or less kinds of polarization spindle angles.

In the imaging device of the second aspect according to the present technology, the first imaging unit may include a polarizer having two kinds of polarization spindle angles, and the two kinds of polarization spindle angles may be orthogonal to each other in the first imaging unit, and the second imaging unit may include a polarizer having two kinds of polarization spindle angles, and the two kinds of polarization spindle angles may be orthogonal to each other in the second imaging unit.

In the imaging device of the second aspect according to the present technology, the first imaging unit may include a polarizer having a polarization spindle angle of 22.5 degrees, and a polarizer having a polarization spindle angle of 112.5 degrees, and the second imaging unit may include a polarizer having a polarization spindle angle of 67.5 degrees, and a polarizer having a polarization spindle angle of 157.5 degrees.

In the imaging device of the second aspect according to the present technology, the first imaging unit may include a polarizer having one kind of polarization spindle angle, the second imaging unit may include a polarizer having one kind of polarization spindle angle, and the difference between the polarization spindle angle of the polarizer included in the first imaging unit and the polarization spindle angle of the polarizer included in the second imaging unit may be not smaller than five degrees and not greater than 85 degrees.

In the imaging device of the second aspect according to the present technology, the first imaging unit may have repeating units including a polarizer and repeating units not including a polarizer, the second imaging unit may have repeating units including a polarizer and repeating units not including a polarizer, and the ratio between the repeating units including a polarizer and the repeating units not including a polarizer in the first imaging unit, and the ratio between the repeating units including a polarizer and the repeating units not including a polarizer in the second imaging unit may be substantially the same.

In the imaging device of the second aspect according to the present technology, the first imaging unit may have repeating units including a polarizer and repeating units not including a polarizer, the second imaging unit may have repeating units including a polarizer and repeating units not including a polarizer, and the layout pattern of the repeating units including a polarizer and the repeating units not including a polarizer in the first imaging unit, and the layout pattern of the repeating units including a polarizer and the repeating units not including a polarizer in the second imaging unit may be substantially the same.

Further, a third aspect of the present technology provides an electronic apparatus including the imaging device of the first aspect or the imaging device of the second aspect according to the present technology.

Effects of the Invention

According to the present technology, it is possible to further increase the accuracy of distance information. Note that effects of the present technology are not limited to the effects described herein, and may include any of the effects described in the present disclosure.

MODE FOR CARRYING OUT THE INVENTION

Figure 1:
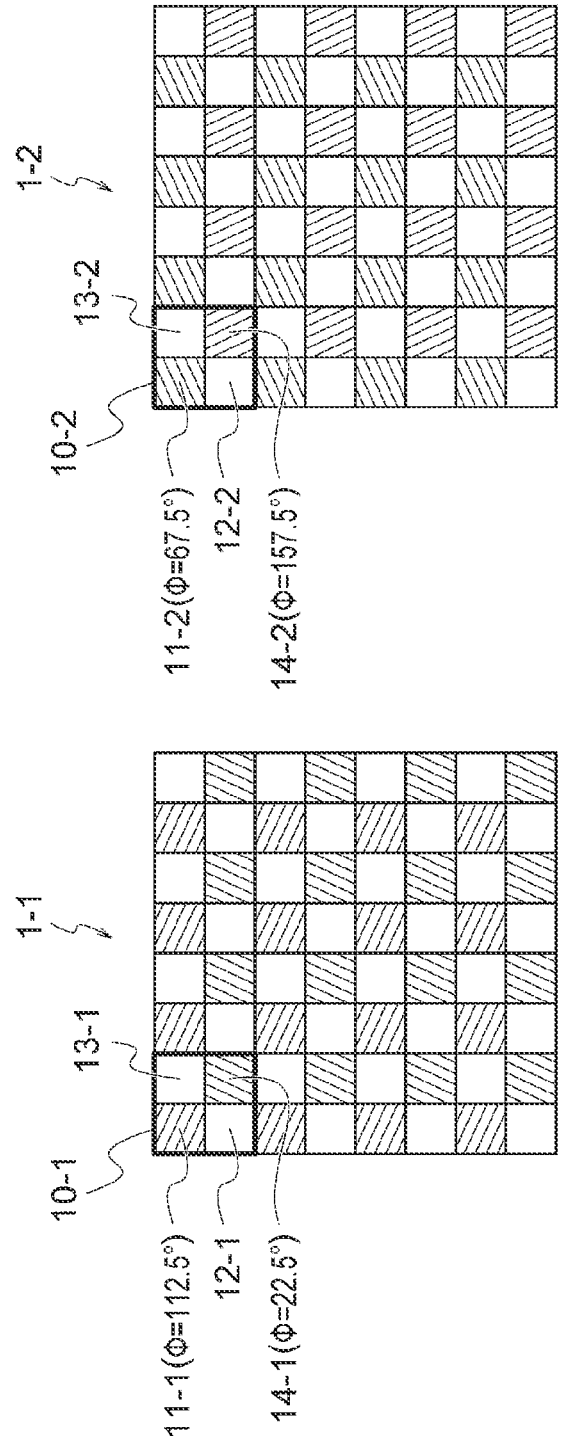
FIG. 1 is a diagram showing example configurations of imaging devices to which the present technology is applied.

The following is a description of preferred embodiments for carrying out the present technology. The embodiments described below are typical examples of embodiments of the present technology, and do not narrow the interpretation of the scope of the present technology. Note that "upper" means an upward direction or the upper side in the drawings, "lower" means a downward direction or the lower side in the drawings, "left" means a leftward direction or the left side in the drawings, and "right" means a rightward direction or the right side in the drawings, unless otherwise specified. Also, in the drawings, the same or equivalent components or members are denoted by the same reference numerals, and explanation of them will not be repeated.

Explanation will be made in the following order.

1. Outline of the present technology
2. First embodiment (Example 1 of an imaging device)
3. Second embodiment (Example 2 of an imaging device)
4. Third embodiment (an example of an electronic apparatus)
5. Examples of use of imaging devices to which the present technology is applied
6. Example application to an endoscopic surgery system
7. Example applications to mobile structures

1. Outline of the Present Technology

First, the outline of the present technology is described.

Polarization sensors can be used to increase distance measurement accuracy. High-precision distance information (3D information) can be obtained from normal information generated from absolute distance information and polarization information. Absolute distance information is required for eliminating indefiniteness at the time of normal calculation. Meanwhile, a method using two polarization sensors might lead to a decrease in sensitivity of absolute distance calculation, because polarized pixels have lower sensitivity than unpolarized pixels.

The present technology has been developed in view of the above circumstances. An imaging device according to the present technology includes a stereo imager. The stereo imager includes a plurality of sensors. Each of the plurality of sensors has an imaging unit formed with a plurality of repeating units, and the imaging unit includes a polarizer having at least one kind of polarization spindle angle. At least two unit images obtained by a plurality of imaging units are combined, to obtain information about polarization in at least three directions and generate normal information. In the imaging device according to the present technology, pixels polarized in at least three directions are not provided in each sensor of a plurality of sensors. Accordingly, the polarized pixels can be reduced, and non-polarized pixels can be provided instead. Thus, sensitivity can be increased. Further, in the imaging device according to the present technology, instead of non-polarized pixels, pixels polarized in a desired direction are provided in each sensor of a plurality of sensors. Accordingly, the resolution of normal information can be increased. As the resolution of normal information becomes higher, the accuracy of the distance direction (the accuracy of 3D information) can be increased.

An imaging device according to the present technology is now described in greater detail.

At least two sensors can be used to obtain distance (absolute distance) information. On the other hand, to generate normal information, information about polarization in at least three directions is necessary. There is no need to obtain polarization in all the directions (four polarization directions, for example) required by each sensor of a plurality of sensors, but polarization is only required to be obtained in all the directions (four polarization directions, for example) required by the entire imaging device (a plurality of sensors). For example, two sensors of the plurality of sensors may be combined to obtain polarization in four directions. Because there is no need to increase the number of polarized pixels more than necessary, and the number of polarized pixels whose sensitivity drops can be reduced, unpolarized pixels (non-polarized pixels) can be used, and sensitivity can be increased accordingly.

In an imaging device according to the present technology, two sensors in which polarizers whose directions are different from each other can be arranged in a horizontal direction and be used, for example. The two sensors arranged in a horizontal direction are combined, so that information about polarization in the directions required to generate normal information is obtained. More specifically, the imaging device according to the present technology calculates an absolute distance from luminance images. In the imaging device according to the present technology, the number of polarized pixels is smaller, and more unpolarized pixels can be used accordingly. Thus, sensitivity becomes higher. Two unit images obtained by two sensors arranged in a horizontal direction are combined, to calculate normal information. With the combination of two unit images, polarization in at least three directions (polarization in four directions, for example) is acquired, and the normal is calculated and generated. Note that, in a case where two sensors are used in an imaging device according to the present technology, for example, the two sensors may be arranged in a horizontal direction, but the arrangement state is not limited to that. Note that the light receiving region of a sensor may be called an imager.

In a case where two sensors are used in distance (absolute distance) calculation in an imaging device according to the present technology, for example, it might be necessary to identify the positions of the pixels that have acquired information about the same position in respective images obtained from a first imager (the light receiving region of a first sensor) and a second imager (the light receiving region of a second sensor). Further, the normal generation can be performed with polarization information about the pixels that are viewing the same site in the first imager (the light receiving region of the first sensor) and the second imager (the light receiving region of the second sensor). To identify the same site (image matching), the images obtained from the first imager (the light receiving region of the first sensor) and the second imager (the light receiving region of the second sensor) preferably have almost the same (or substantially the same) degrees of luminance.

In the case described above, the number of sensors constituting an imaging device according to the present technology is two. However, the present technology is not limited to that, and the number of sensors constituting an imaging device according to the present technology may be three, or may be four or larger. Further, to generate normal information, an imaging device according to the present technology may combine at least two unit images obtained by the respective imaging units of a plurality of imaging units constituting each sensor of a plurality of sensors. That is, an imaging device according to the present technology may generate normal information by combining all of the unit images obtained by the respective imaging units of a plurality of imaging units constituting each sensor of a plurality of sensors, or may generate normal information by combining some of the unit images obtained by the respective imaging units of a plurality of imaging units constituting each sensor of a plurality of sensors.

Next, to explain the present technology more specifically, embodiments according to the present technology are described below in detail.

2. First Embodiment (Example 1 of an Imaging Device)

An imaging device of a first embodiment (Example 1 of an imaging device) according to the present technology is an imaging device that includes a stereo imager. The stereo imager includes a first sensor and a second sensor. The first sensor has a first imaging unit formed with a plurality of repeating units, and the second sensor has a second imaging unit formed with a plurality of repeating units. The first imaging unit includes a polarizer having at least one kind of polarization spindle angle, and the second imaging unit includes a polarizer having at least one kind of polarization spindle angle. A first unit image obtained by the first imaging unit and a second unit image obtained by the second imaging unit are combined, so that information about polarization in at least three directions is acquired, and normal information is generated. That is, the imaging device of the first embodiment according to the present technology acquires information about polarization in at least three directions and generates normal information, using two sensors. In the imaging device of the first embodiment according to the present technology, to generate normal information, it is only required to acquire information about polarization in at least three directions. Therefore, the information about polarization may be information about polarization in three directions, information about polarization in four directions, or information about polarization in five or more directions.

With the imaging device of the first embodiment according to the present technology, it is possible to further increase the accuracy of distance information. More specifically, with the imaging device of the first embodiment according to the present technology, pixels polarized in at least three directions are not provided in the respective sensors of a plurality of (two) sensors. Accordingly, polarized pixels can be reduced, and non-polarized pixels can be provided instead. Thus, sensitivity can be increased. Further, instead of non-polarized pixels, pixels polarized in a desired direction may be provided in each sensor of the plurality of (two) sensors. Thus, the resolution of normal information can be increased. As the resolution of normal information becomes higher, the accuracy of the distance direction (the accuracy of 3D information) can be increased.

In the imaging device of the first embodiment according to the present technology, a polarizer having at least one kind of polarization spindle angle of the first imaging unit, and a polarizer having at least one kind of polarization spindle angle of the second imaging unit preferably differ from each other in polarization spindle angle. It is preferable that the second imaging unit does not include the polarizer having at least one kind of polarization spindle angle of the first imaging unit.

In the imaging device of the first embodiment according to the present technology, the first unit image and the second unit image are preferably reconstructed on the basis of the stereo correspondence relationship.

In the imaging device of the first embodiment according to the present technology, the first imaging unit preferably includes a polarizer having two or less kinds of polarization spindle angles, and the second imaging unit preferably includes a polarizer having two or less kinds of polarization spindle angles.

In the imaging device of the first embodiment according to the present technology, the first imaging unit preferably includes a polarizer having two kinds of polarization spindle angles, and the two kinds of polarization spindle angles are preferably orthogonal to each other in the first imaging unit. The second imaging unit preferably includes a polarizer having two kinds of polarization spindle angles, and the two kinds of polarization spindle angles are preferably orthogonal to each other in the second imaging unit.

In the imaging device of the first embodiment according to the present technology, the first imaging unit preferably includes a polarizer having a polarization spindle angle of 22.5 degrees and a polarizer having a polarization spindle angle of 112.5 degrees, and the second imaging unit preferably includes a polarizer having a polarization spindle angle of 67.5 degrees and a polarizer having a polarization spindle angle of 157.5 degrees.

In the imaging device of the first embodiment according to the present technology, the first imaging unit preferably includes a polarizer having one kind of polarization spindle angle, and the second imaging unit preferably includes a polarizer having one kind of polarization spindle angle. The difference between the polarization spindle angle of the polarizer included in the first imaging unit and the polarization spindle angle of the polarizer included in the second imaging unit is preferably not smaller than five degrees and not greater than 85 degrees.

In the imaging device of the first embodiment according to the present technology, the first imaging unit preferably has repeating units including polarizers and repeating units not including polarizers, and the second imaging unit preferably has repeating units including polarizers and repeating units not including polarizers. The ratio between the repeating units including polarizers and the repeating units not including polarizers in the first imaging unit, and the ratio between the repeating units including polarizers and the repeating units not including polarizers in the second imaging unit are preferably substantially the same.

In the imaging device of the first embodiment according to the present technology, the first imaging unit preferably has repeating units including polarizers and repeating units not including polarizers, and the second imaging unit preferably has repeating units including polarizers and repeating units not including polarizers. The layout pattern of the repeating units including polarizers and the repeating units not including polarizers in the first imaging unit, and the layout pattern of the repeating units including polarizers and the repeating units not including polarizers in the second imaging unit are preferably substantially the same.

In the description below, imaging devices of the first embodiment according to the present technology are explained in greater detail, with reference to FIGS. 1 to 9 and FIGS. 11, 12, 13, 14, 15, 16, 17, 18, 19, 20A, 20B, 21A, 21B, 21C, 21D, and 22.

Figure 16:
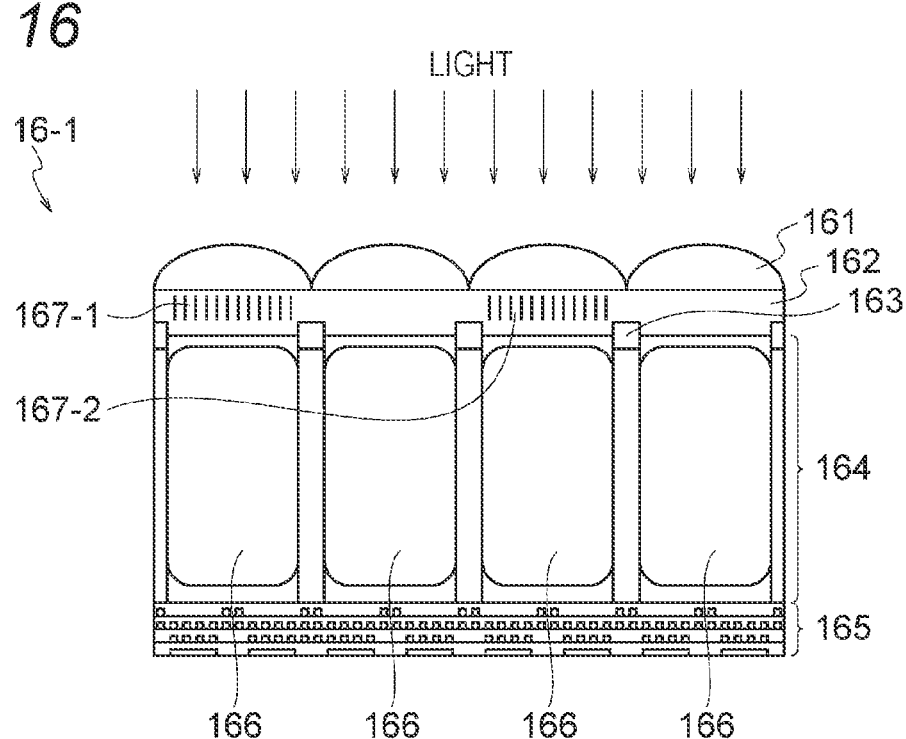
FIG. 16 is a cross-sectional view showing an example configuration of a sensor forming an imaging device to which the present technology is applied.
Figure 17:
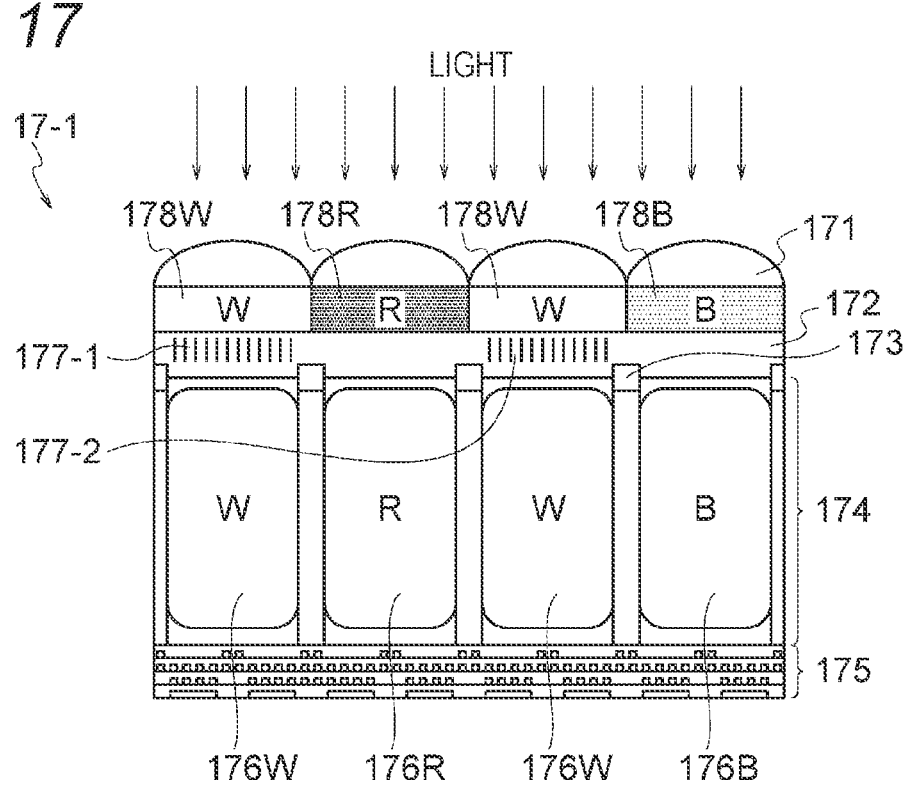
FIG. 17 is a cross-sectional view showing an example configuration of a sensor forming an imaging device to which the present technology is applied.
Figure 18:
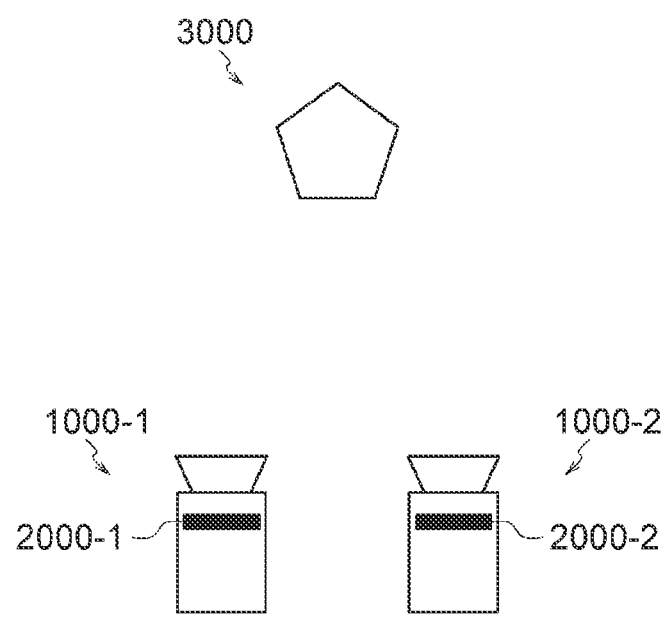
FIG. 18 is a diagram showing an example imaging mode using an imaging device to which the present technology is applied.
Figure 19:
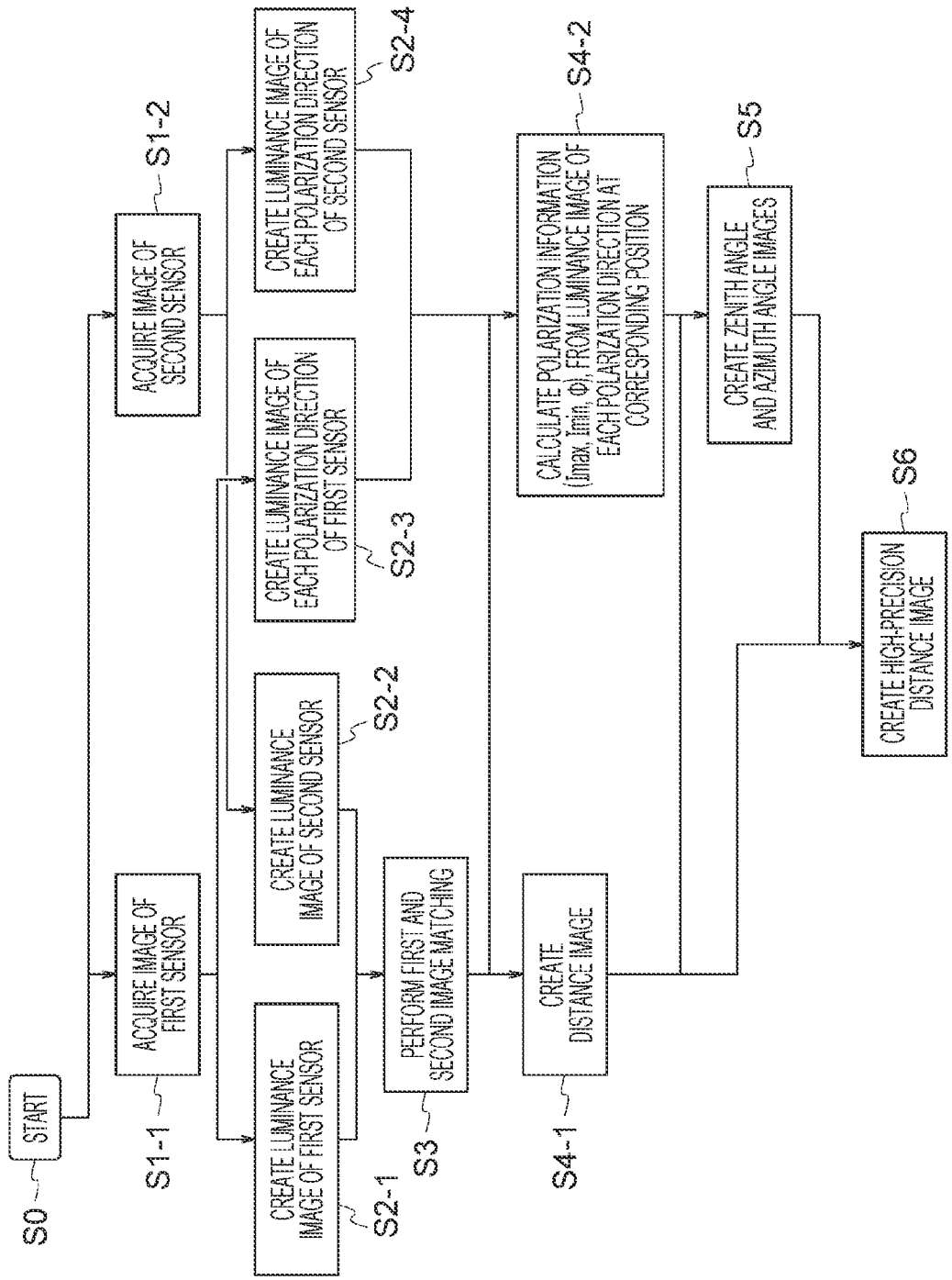
FIG. 19 is a flowchart showing the flow in a process to be performed by an imaging device to which the present technology is applied.

FIGS. 1 to 9 and FIGS. 11 to 15 are diagrams showing example configurations of imaging devices of the first embodiment according to the present technology. FIGS. 16 and 17 are cross-sectional views each showing an example configuration of a sensor, or more specifically, an imager that is the light receiving region of a sensor forming an imaging device of the first embodiment according to the present technology. FIG. 18 is a diagram showing an example imaging mode in which an imaging device of the first embodiment according to the present technology is used. FIG. 19 is a flowchart showing the flow in a process to be performed by an imaging device of the first embodiment according to the present technology. FIGS. 20A, 20B, 21A, 21B, 21C, 21D, 22, 23, and 24 are diagrams for explaining that an imaging device of the first embodiment according to the present technology is used to generate normal information and obtain a distance image (3D information).

First, explanation is made with reference to FIGS. 1 to 9 and FIGS. 11 to 15.

FIG. 1 shows an imaging device 1. The imaging device 1 includes a first sensor 1-1 and a second sensor 1-2. That is, the stereo imager included in the imaging device 1 is formed with the first sensor 1-1 and the second sensor 1-2.

The first sensor 1-1 has an imaging unit 10-1 formed with four repeating units 11-1 to 14-1. The repeating unit 11-1 includes a polarizer having a polarization spindle angle of 112.5 degrees and one pixel, and the repeating unit 11-1 obtains a polarized luminance value of the one pixel. The repeating unit 12-1 includes one pixel without a polarizer, and the repeating unit 12-1 obtains an unpolarized luminance value of the one pixel. The repeating unit 13-1 includes one pixel without a polarizer, and the repeating unit 13-1 obtains an unpolarized luminance value of the one pixel. The repeating unit 14-1 includes a polarizer having a polarization spindle angle of 22.5 degrees and one pixel, and the repeating unit 14-1 obtains a polarized luminance value of the one pixel.

The second sensor 1-2 has an imaging unit 10-2 formed with four repeating units 11-2 to 14-2. The repeating unit 11-2 includes a polarizer having a polarization spindle angle of 67.5 degrees and one pixel, and the repeating unit 11-2 obtains a polarized luminance value of the one pixel. The repeating unit 12-2 includes one pixel without a polarizer, and the repeating unit 12-2 obtains an unpolarized luminance value of the one pixel. The repeating unit 13-2 includes one pixel without a polarizer, and the repeating unit 13-2 obtains an unpolarized luminance value of the one pixel. The repeating unit 14-2 includes a polarizer having a polarization spindle angle of 157.5 degrees and one pixel, and the repeating unit 14-2 obtains a polarized luminance value of the one pixel.

As shown in FIG. 1, the arrangement of polarized pixels and non-polarized pixels (unpolarized pixels) is the same in both sensors. Each polarizer is symmetrical to each corresponding pixel and has the same length, and it is possible to obtain a luminance not dependent on polarization by adding up the luminances of pixels whose angles are orthogonal to each other. Accordingly, the sensitivities of unit images obtained by the imaging units 10-1 and 10-2 are substantially the same, and the same sites can be easily identified. It is also easy to calculate normal information.

Figure 2:
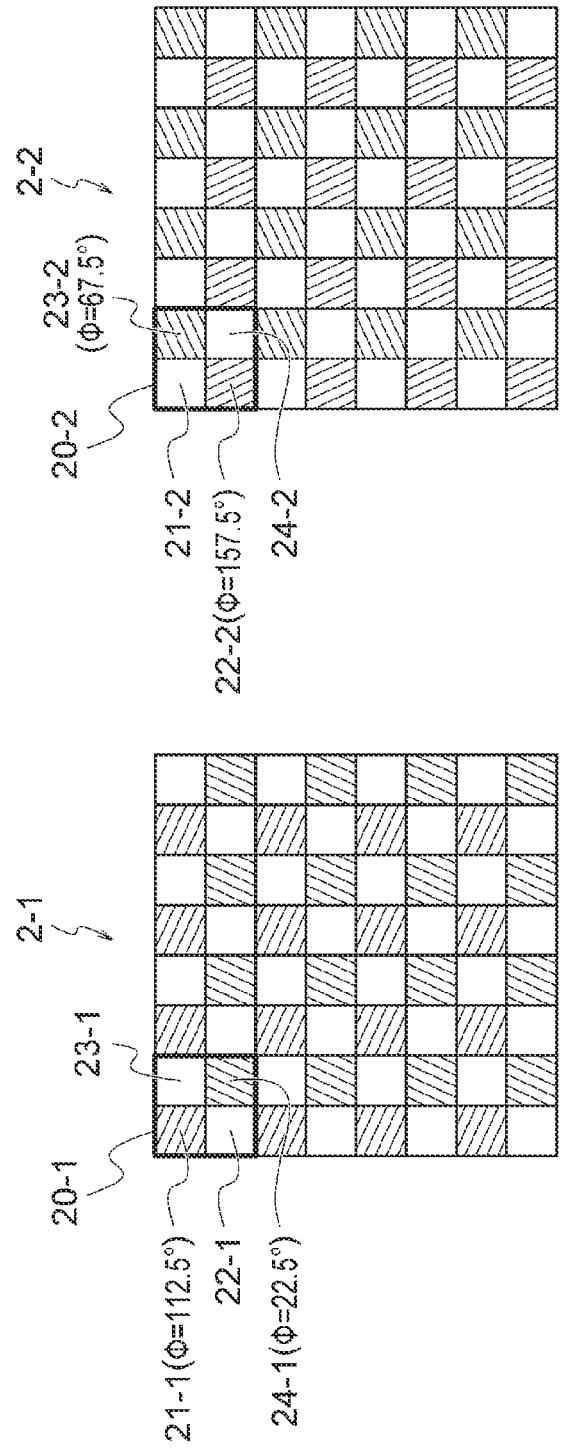
FIG. 2 is a diagram showing example configurations of imaging devices to which the present technology is applied.

FIG. 2 shows an imaging device 2. The imaging device 2 includes a first sensor 2-1 and a second sensor 2-2. That is, the stereo imager included in the imaging device 2 is formed with the first sensor 2-1 and the second sensor 2-2.

The first sensor 2-1 has an imaging unit 20-1 formed with four repeating units 21-1 to 24-1. The repeating unit 21-1 includes a polarizer having a polarization spindle angle of 112.5 degrees and one pixel, and the repeating unit 21-1 obtains a polarized luminance value of the one pixel. The repeating unit 22-1 includes one pixel without a polarizer, and the repeating unit 22-1 obtains an unpolarized luminance value of the one pixel. The repeating unit 23-1 includes one pixel without a polarizer, and the repeating unit 23-1 obtains an unpolarized luminance value of the one pixel. The repeating unit 24-1 includes a polarizer having a polarization spindle angle of 22.5 degrees and one pixel, and the repeating unit 24-1 obtains a polarized luminance value of the one pixel.

The second sensor 2-2 has an imaging unit 20-2 formed with four repeating units 21-2 to 24-2. The repeating unit 21-2 includes one pixel without a polarizer, and the repeating unit 21-2 obtains an unpolarized luminance value of the one pixel. The repeating unit 22-2 includes a polarizer having a polarization spindle angle of 157.5 degrees and one pixel, and the repeating unit 22-2 obtains a polarized luminance value of the one pixel. The repeating unit 23-2 includes a polarizer having a polarization spindle angle of 67.5 degrees and one pixel, and the repeating unit 23-2 obtains a polarized luminance value of the one pixel. The repeating unit 24-2 includes one pixel without a polarizer, and the repeating unit 24-2 obtains an unpolarized luminance value of the one pixel.

As shown in FIG. 2, the spindle angle of the polarizer is the same as that of the imaging device 1 shown in FIG. 1, but the arrangement of the polarized pixels and the non-polarized pixels differ from that of the imaging device 1. The effects of the imaging device 2 are similar to the effects of the imaging device 1.

Figure 3:
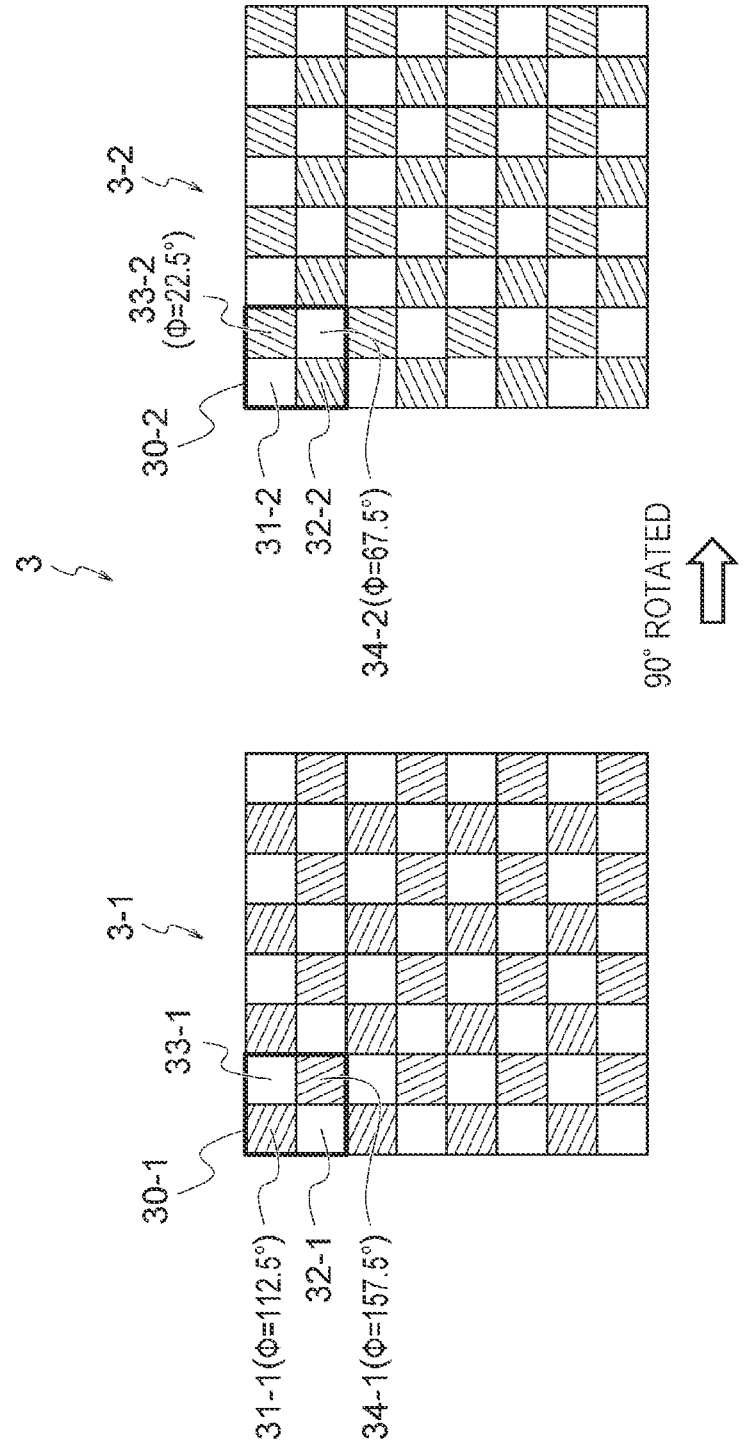
FIG. 3 is a diagram showing example configurations of imaging devices to which the present technology is applied.

FIG. 3 shows an imaging device 3. The imaging device 3 includes a first sensor 3-1 and a second sensor 3-2. That is, the stereo imager included in the imaging device 3 is formed with the first sensor 3-1 and the first sensor 3-2.

The first sensor 3-1 has an imaging unit 30-1 formed with four repeating units 31-1 to 34-1. The repeating unit 31-1 includes a polarizer having a polarization spindle angle of 112.5 degrees and one pixel, and the repeating unit 31-1 obtains a polarized luminance value of the one pixel. The repeating unit 32-1 includes one pixel without a polarizer, and the repeating unit 32-1 obtains an unpolarized luminance value of the one pixel. The repeating unit 33-1 includes one pixel without a polarizer, and the repeating unit 23-1 obtains an unpolarized luminance value of the one pixel. The repeating unit 34-1 includes a polarizer having a polarization spindle angle of 157.5 degrees and one pixel, and the repeating unit 34-1 obtains a polarized luminance value of the one pixel.

The second sensor 3-2 has an imaging unit 30-2 formed with four repeating units 31-2 to 34-2. The repeating unit 31-2 includes one pixel without a polarizer, and the repeating unit 31-2 obtains an unpolarized luminance value of the one pixel. The repeating unit 32-2 includes a polarizer having a polarization spindle angle of 67.5 degrees and one pixel, and the repeating unit 32-2 obtains a polarized luminance value of the one pixel. The repeating unit 33-2 includes a polarizer having a polarization spindle angle of 22.5 degrees and one pixel, and the repeating unit 33-2 obtains a polarized luminance value of the one pixel. The repeating unit 34-2 includes one pixel without a polarizer, and the repeating unit 34-2 obtains an unpolarized luminance value of the one pixel.

The configuration of the imaging device 3 is included in the configuration of the imaging device 2, but can be realized by rotating the sensor of one type. As the same sensors can be used, the manufacturing costs are effectively lowered.

Figure 4:
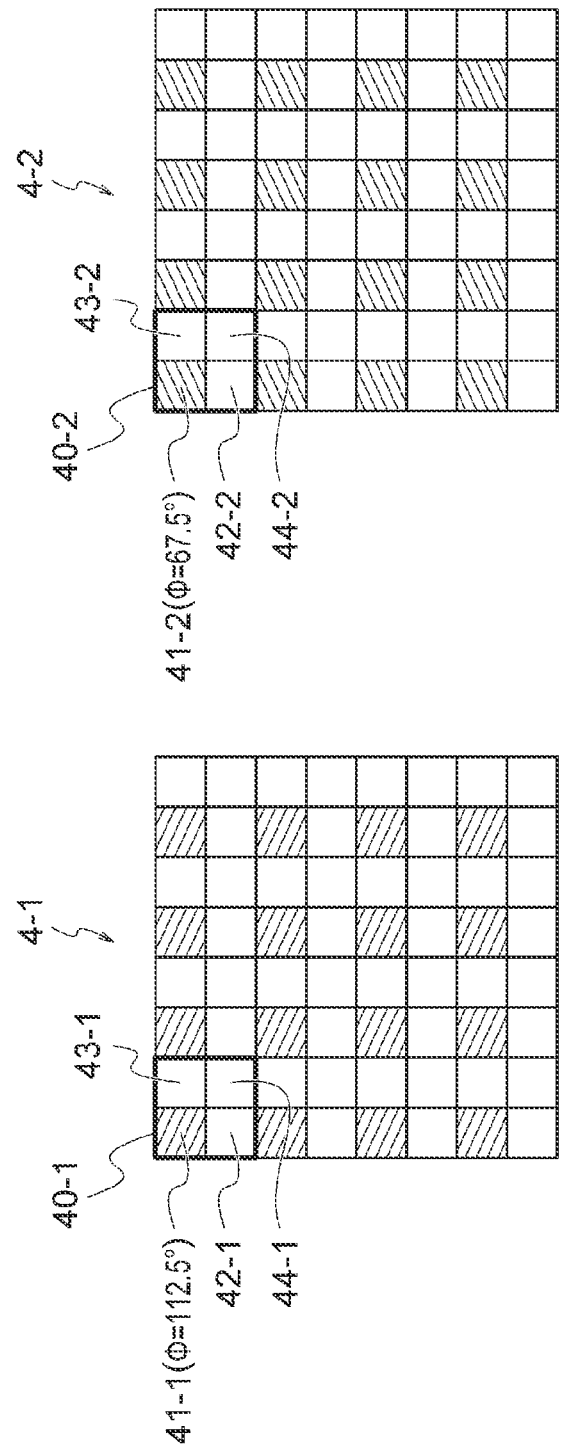
FIG. 4 is a diagram showing example configurations of imaging devices to which the present technology is applied.

FIG. 4 shows an imaging device 4. The imaging device 4 includes a first sensor 4-1 and a second sensor 4-2. That is, the stereo imager included in the imaging device 4 is formed with the first sensor 4-1 and the second sensor 4-2.

The first sensor 4-1 has an imaging unit 40-1 formed with four repeating units 41-1 to 44-1. The repeating unit 41-1 includes a polarizer having a polarization spindle angle of 112.5 degrees and one pixel, and the repeating unit 41-1 obtains a polarized luminance value of the one pixel. The repeating unit 42-1 includes one pixel without a polarizer, and the repeating unit 42-1 obtains an unpolarized luminance value of the one pixel. The repeating unit 43-1 includes one pixel without a polarizer, and the repeating unit 43-1 obtains an unpolarized luminance value of the one pixel. The repeating unit 44-1 includes one pixel without polarization, and the repeating unit 44-1 obtains an unpolarized luminance value of the one pixel.

The second sensor 4-2 has an imaging unit 40-2 formed with four repeating units 41-2 to 44-2. The repeating unit 41-2 includes a polarizer having a polarization spindle angle of 67.5 degrees and one pixel, and the repeating unit 41-2 obtains a polarized luminance value of the one pixel. The repeating unit 42-2 includes one pixel without a polarizer, and the repeating unit 42-2 obtains an unpolarized luminance value of the one pixel. The repeating unit 43-2 includes one pixel without a polarizer, and the repeating unit 43-2 obtains an unpolarized luminance value of the one pixel. The repeating unit 44-2 includes one pixel without polarization, and the repeating unit 44-2 obtains an unpolarized luminance value of the one pixel.

Polarizers of only one type exist in each of the first sensors 4-1 and 4-2, and the polarization component in a direction perpendicular to the component that can be acquired by the polarized pixels is calculated from the difference between the non-polarized pixels and the polarized pixels. As a larger number of polarized pixels can be included, the sensitivity of luminance images can be increased.

Figure 5:
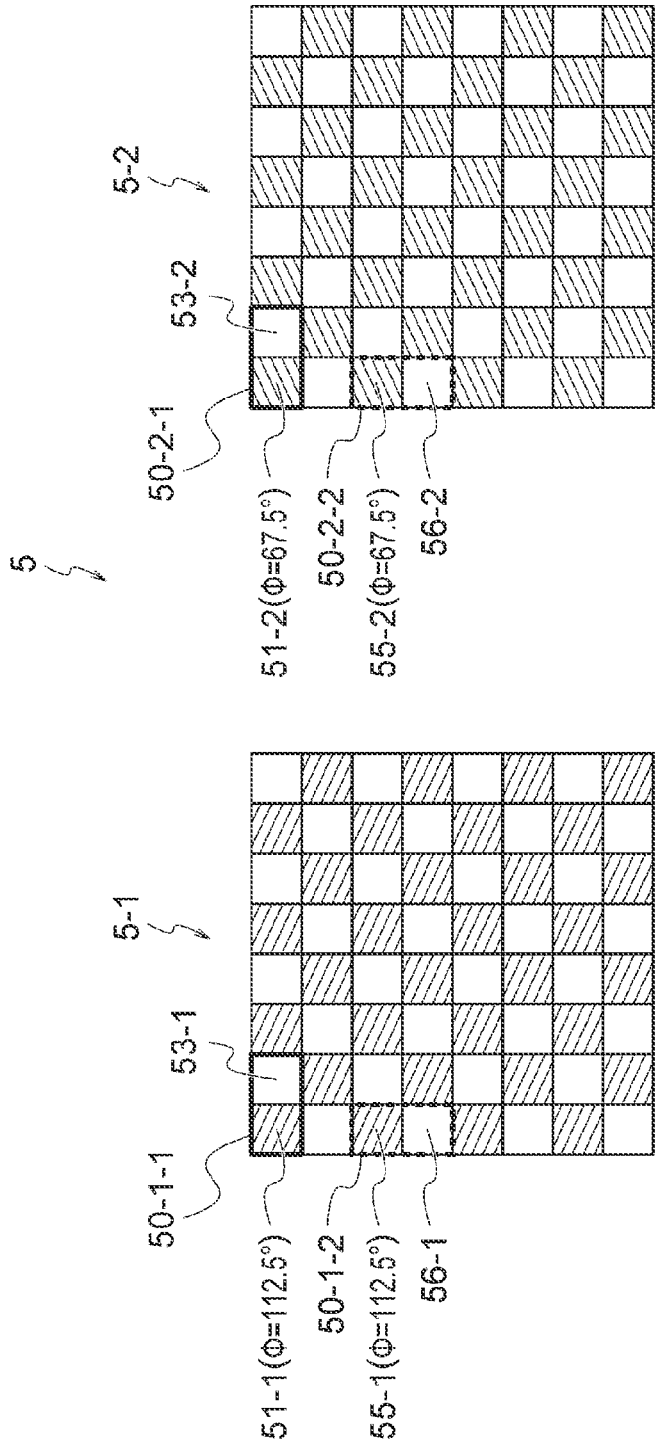
FIG. 5 is a diagram showing example configurations of imaging devices to which the present technology is applied.

FIG. 5 shows an imaging device 5. The imaging device 5 includes a first sensor 5-1 and a second sensor 5-2. That is, the stereo imager included in the imaging device 5 is formed with the first sensor 5-1 and the second sensor 5-2.

The first sensor 5-1 has an imaging unit 50-1-1 formed with two repeating units 51-1 and 53-1 arranged in a horizontal direction (a horizontal direction in FIG. 5). The repeating unit 51-1 includes a polarizer having a polarization spindle angle of 112.5 degrees and one pixel, and the repeating unit 51-1 obtains a polarized luminance value of the one pixel. The repeating unit 53-1 includes one pixel without a polarizer, and the repeating unit 53-1 obtains an unpolarized luminance value of the one pixel. The first sensor 5-1 also has an imaging unit 50-1-2 formed with two repeating units 55-1 and 56-1 arranged in a vertical direction (a vertical direction in FIG. 5). The repeating unit 55-1 includes a polarizer having a polarization spindle angle of 112.5 degrees and one pixel, and the repeating unit 55-1 obtains a polarized luminance value of the one pixel. The repeating unit 56-1 includes one pixel without a polarizer, and the repeating unit 56-1 obtains an unpolarized luminance value of the one pixel.

The second sensor 5-2 has an imaging unit 50-2-1 formed with two repeating units 51-2 and 53-2 arranged in a horizontal direction (a horizontal direction in FIG. 5). The repeating unit 51-2 includes a polarizer having a polarization spindle angle of 67.5 degrees and one pixel, and the repeating unit 51-2 obtains a polarized luminance value of the one pixel. The repeating unit 53-2 includes one pixel without a polarizer, and the repeating unit 53-2 obtains an unpolarized luminance value of the one pixel. The first sensor 5-2 also has an imaging unit 50-2-2 formed with two repeating units 55-2 and 56-2 arranged in a vertical direction (a vertical direction in FIG. 5). The repeating unit 55-2 includes a polarizer having a polarization spindle angle of 67.5 degrees and one pixel, and the repeating unit 55-2 obtains a polarized luminance value of the one pixel. The repeating unit 56-2 includes one pixel without a polarizer, and the repeating unit 56-2 obtains an unpolarized luminance value of the one pixel.

The imaging device 5 has a larger number of polarized pixels (repeating units each having a polarizer) than the imaging device 4. The imaging device 5 can have a higher horizontal resolution, a higher vertical resolution, or both a higher horizontal resolution and a higher vertical resolution than the imaging device 4.

Figure 6:
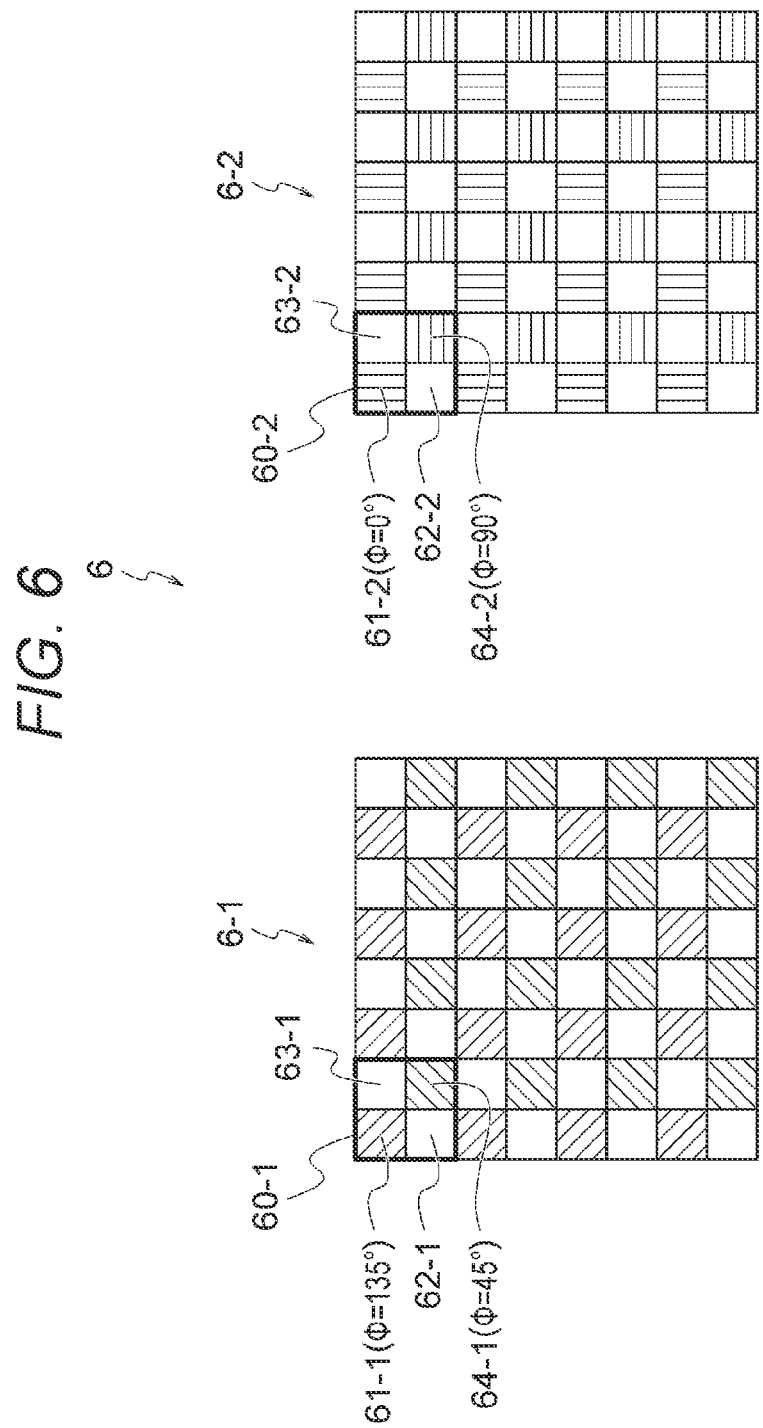
FIG. 6 is a diagram showing example configurations of imaging devices to which the present technology is applied.

FIG. 6 shows an imaging device 6. The imaging device 6 includes a first sensor 6-1 and a second sensor 6-2. That is, the stereo imager included in the imaging device 6 is formed with the first sensor 6-1 and the second sensor 6-2.

The first sensor 6-1 has an imaging unit 60-1 formed with four repeating units 61-1 to 64-1. The repeating unit 61-1 includes a polarizer having a polarization spindle angle of 135 degrees and one pixel, and the repeating unit 61-1 obtains a polarized luminance value of the one pixel. The repeating unit 62-1 includes one pixel without a polarizer, and the repeating unit 62-1 obtains an unpolarized luminance value of the one pixel. The repeating unit 63-1 includes one pixel without a polarizer, and the repeating unit 63-1 obtains an unpolarized luminance value of the one pixel. The repeating unit 64-1 includes a polarizer having a polarization spindle angle of 45 degrees and one pixel, and the repeating unit 64-1 obtains a polarized luminance value of the one pixel.

The second sensor 6-2 has an imaging unit 60-2 formed with four repeating units 61-2 to 64-2. The repeating unit 61-2 includes a polarizer having a polarization spindle angle of 0 degrees and one pixel, and the repeating unit 61-2 obtains a polarized luminance value of the one pixel. The repeating unit 62-2 includes one pixel without a polarizer, and the repeating unit 62-2 obtains an unpolarized luminance value of the one pixel. The repeating unit 63-2 includes one pixel without a polarizer, and the repeating unit 63-2 obtains an unpolarized luminance value of the one pixel. The repeating unit 64-2 includes a polarizer having a polarization spindle angle of 90 degrees and one pixel, and the repeating unit 64-2 obtains a polarized luminance value of the one pixel.

The imaging device 6 differs from the imaging device 1 in that polarizers having polarization spindle angles orthogonal to each other are disposed in each sensor, and the configuration thereof involves angles other than 22.5 degrees/112.5 degrees and 67.5 degrees/157.5 degrees. With this combination of polarizers, variations similar to the imaging devices 2 to 5 can also be formed.

Figure 7:
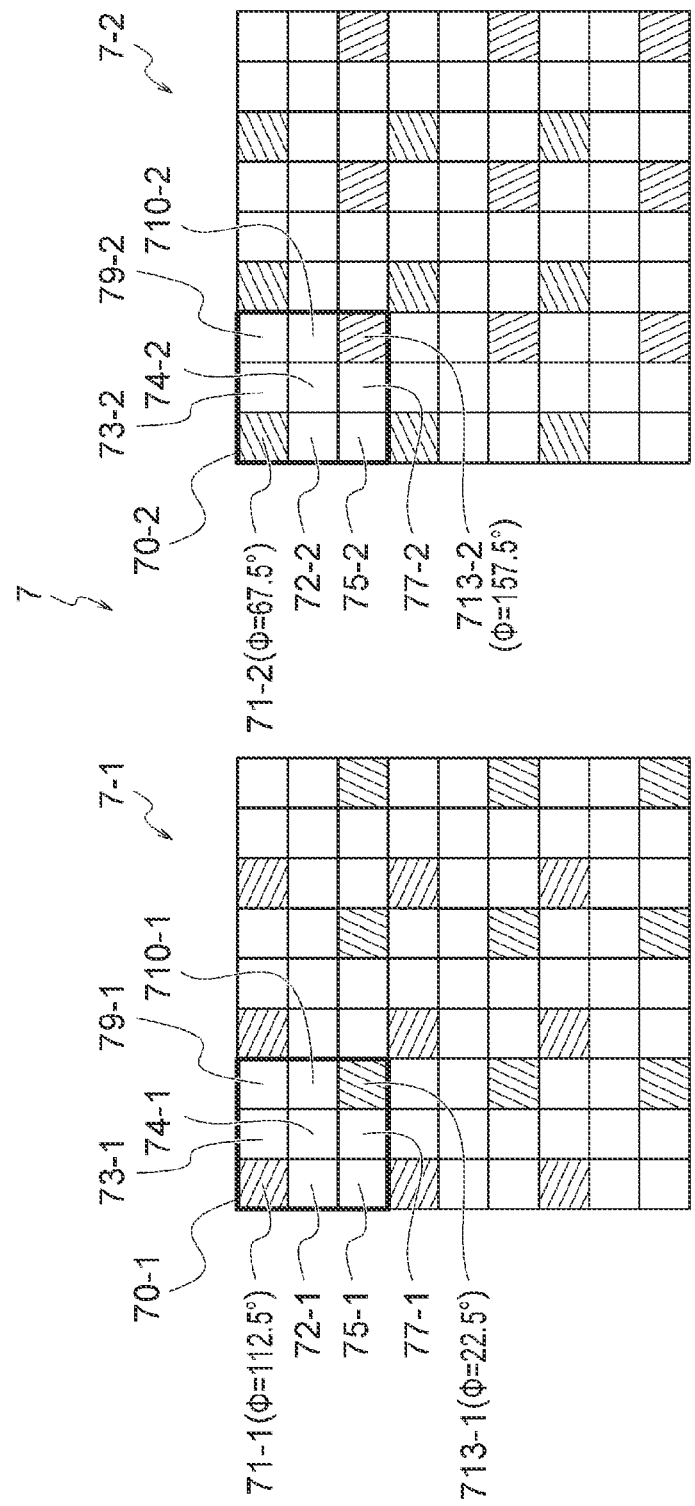
FIG. 7 is a diagram showing example configurations of imaging devices to which the present technology is applied.

FIG. 7 shows an imaging device 7. The imaging device 7 includes a first sensor 7-1 and a second sensor 7-2. That is, the stereo imager included in the imaging device 7 is formed with the first sensor 7-1 and the second sensor 7-2.

The first sensor 7-1 has an imaging unit 70-1 formed with nine (3×3) repeating units 71-1 to 74-1, 77-1, 79-1, 710-1, and 713-1. The repeating unit 71-1 includes a polarizer having a polarization spindle angle of 112.5 degrees and one pixel, and the repeating unit 71-1 obtains a polarized luminance value of the one pixel. The repeating unit 72-1 includes one pixel without a polarizer, and the repeating unit 72-1 obtains an unpolarized luminance value of the one pixel. The repeating unit 73-1 includes one pixel without a polarizer, and the repeating unit 73-1 obtains an unpolarized luminance value of the one pixel. The repeating unit 74-1 includes one pixel without a polarizer, and the repeating unit 74-1 obtains an unpolarized luminance value of the one pixel. The repeating unit 77-1 includes one pixel without a polarizer, and the repeating unit 77-1 obtains an unpolarized luminance value of the one pixel. The repeating unit 79-1 includes one pixel without a polarizer, and the repeating unit 79-1 obtains an unpolarized luminance value of the one pixel. The repeating unit 710-1 includes one pixel without a polarizer, and the repeating unit 710-1 obtains an unpolarized luminance value of the one pixel. The repeating unit 713-1 includes a polarizer having a polarization spindle angle of 22.5 degrees and one pixel, and the repeating unit 713-1 obtains a polarized luminance value of the one pixel.

The first sensor 7-2 has an imaging unit 70-2 formed with nine (3×3) repeating units 71-2 to 74-2, 77-2, 79-2, 710-2, and 713-2. The repeating unit 71-2 includes a polarizer having a polarization spindle angle of 67.5 degrees and one pixel, and the repeating unit 71-2 obtains a polarized luminance value of the one pixel. The repeating unit 72-2 includes one pixel without a polarizer, and the repeating unit 72-2 obtains an unpolarized luminance value of the one pixel. The repeating unit 73-2 includes one pixel without a polarizer, and the repeating unit 73-2 obtains an unpolarized luminance value of the one pixel. The repeating unit 74-2 includes one pixel without a polarizer, and the repeating unit 74-2 obtains an unpolarized luminance value of the one pixel. The repeating unit 77-2 includes one pixel without a polarizer, and the repeating unit 77-2 obtains an unpolarized luminance value of the one pixel. The repeating unit 79-2 includes one pixel without a polarizer, and the repeating unit 79-2 obtains an unpolarized luminance value of the one pixel. The repeating unit 710-2 includes one pixel without a polarizer, and the repeating unit 710-2 obtains an unpolarized luminance value of the one pixel. The repeating unit 713-2 includes a polarizer having a polarization spindle angle of 157.5 degrees and one pixel, and the repeating unit 713-2 obtains a polarized luminance value of the one pixel.

As described above, the imaging device 7 is an example in which a unit image (imaging unit) is 3×3. The sensitivity of luminance images can be further increased. In this manner, a unit image is not limited to 2×2.

Figure 8:
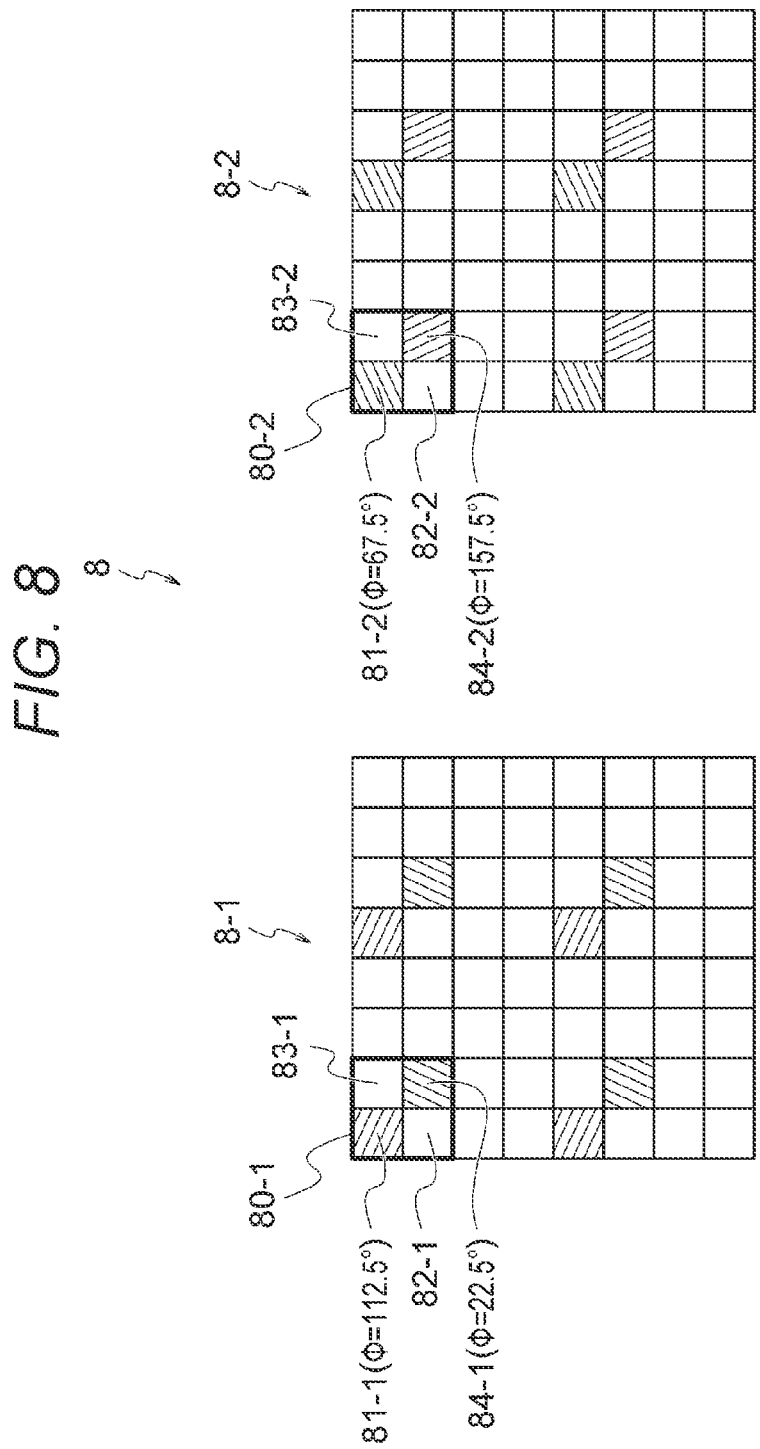
FIG. 8 is a diagram showing example configurations of imaging devices to which the present technology is applied.

FIG. 8 shows an imaging device 8. The imaging device 8 includes a first sensor 8-1 and a second sensor 8-2. That is, the stereo imager included in the imaging device 8 is formed with the first sensor 8-1 and the second sensor 8-2.

The first sensor 8-1 has an imaging unit 80-1 formed with four repeating units 81-1 to 84-1. The repeating unit 81-1 includes a polarizer having a polarization spindle angle of 112.5 degrees and one pixel, and the repeating unit 81-1 obtains a polarized luminance value of the one pixel. The repeating unit 82-1 includes one pixel without a polarizer, and the repeating unit 82-1 obtains an unpolarized luminance value of the one pixel. The repeating unit 83-1 includes one pixel without a polarizer, and the repeating unit 83-1 obtains an unpolarized luminance value of the one pixel. The repeating unit 84-1 includes a polarizer having a polarization spindle angle of 22.5 degrees and one pixel, and the repeating unit 84-1 obtains a polarized luminance value of the one pixel.

The second sensor 8-2 has an imaging unit 80-2 formed with four repeating units 81-2 to 84-2. The repeating unit 81-2 includes a polarizer having a polarization spindle angle of 67.5 degrees and one pixel, and the repeating unit 81-2 obtains a polarized luminance value of the one pixel. The repeating unit 82-2 includes one pixel without a polarizer, and the repeating unit 82-2 obtains an unpolarized luminance value of the one pixel. The repeating unit 83-2 includes one pixel without a polarizer, and the repeating unit 83-2 obtains an unpolarized luminance value of the one pixel. The repeating unit 84-2 includes a polarizer having a polarization spindle angle of 157.5 degrees and one pixel, and the repeating unit 84-2 obtains a polarized luminance value of the one pixel.

As shown in FIG. 8, the imaging device 8 does not have unit pixels arranged in a repetitive manner, but has unit pixels arranged at specific positions (in a pattern). The sensitivity of luminance images can be further increased. In this manner, polarized pixels can be freely arranged.

Figure 9:
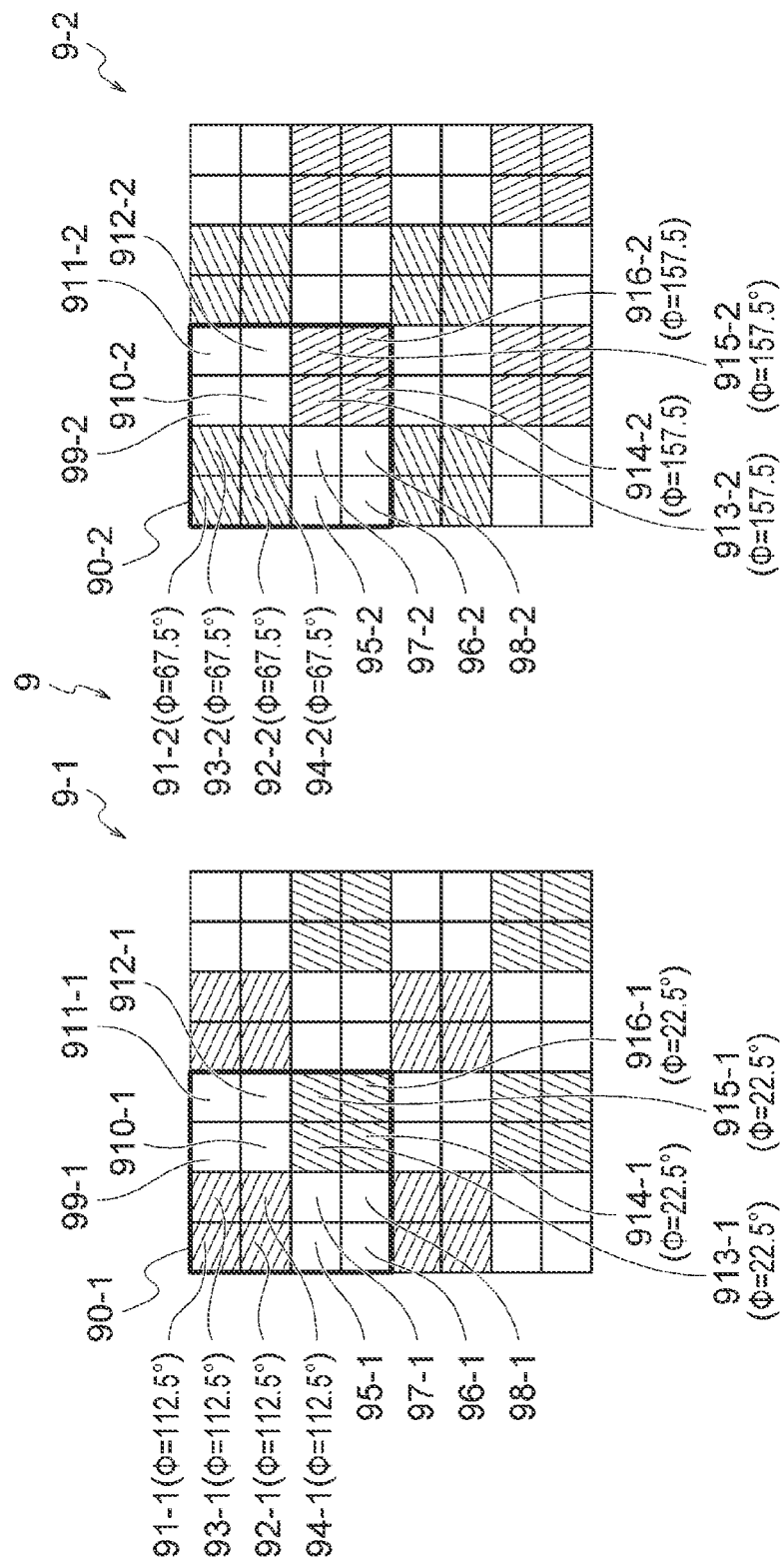
FIG. 9 is a diagram showing example configurations of imaging devices to which the present technology is applied.

FIG. 9 shows an imaging device 9. The imaging device 9 includes a first sensor 9-1 and a second sensor 9-2. That is, the stereo imager included in the imaging device 9 is formed with the first sensor 9-1 and the second sensor 9-2.

The first sensor 9-1 has an imaging unit 90-1 formed with 16 (4×4) repeating units 91-1 to 916-1. The repeating unit 91-1 includes a polarizer having a polarization spindle angle of 112.5 degrees and one pixel, and the repeating unit 91-1 obtains a polarized luminance value of the one pixel. The repeating unit 92-1 includes a polarizer having a polarization spindle angle of 112.5 degrees and one pixel, and the repeating unit 92-1 obtains a polarized luminance value of the one pixel. The repeating unit 93-1 includes a polarizer having a polarization spindle angle of 112.5 degrees and one pixel, and the repeating unit 93-1 obtains a polarized luminance value of the one pixel. The repeating unit 94-1 includes a polarizer having a polarization spindle angle of 112.5 degrees and one pixel, and the repeating unit 94-1 obtains a polarized luminance value of the one pixel.

The repeating unit 95-1 includes one pixel without a polarizer, and the repeating unit 95-1 obtains an unpolarized luminance value of the one pixel. The repeating unit 96-1 includes one pixel without a polarizer, and the repeating unit 96-1 obtains an unpolarized luminance value of the one pixel. The repeating unit 97-1 includes one pixel without a polarizer, and the repeating unit 97-1 obtains an unpolarized luminance value of the one pixel. The repeating unit 98-1 includes one pixel without a polarizer, and the repeating unit 98-1 obtains an unpolarized luminance value of the one pixel.

The repeating unit 99-1 includes one pixel without a polarizer, and the repeating unit 99-1 obtains an unpolarized luminance value of the one pixel. The repeating unit 910-1 includes one pixel without a polarizer, and the repeating unit 910-1 obtains an unpolarized luminance value of the one pixel. The repeating unit 911-1 includes one pixel without a polarizer, and the repeating unit 911-1 obtains an unpolarized luminance value of the one pixel. The repeating unit 912-1 includes one pixel without a polarizer, and the repeating unit 912-1 obtains an unpolarized luminance value of the one pixel.

The repeating unit 913-1 includes a polarizer having a polarization spindle angle of 22.5 degrees and one pixel, and the repeating unit 913-1 obtains a polarized luminance value of the one pixel. The repeating unit 914-1 includes a polarizer having a polarization spindle angle of 22.5 degrees and one pixel, and the repeating unit 914-1 obtains a polarized luminance value of the one pixel. The repeating unit 915-1 includes a polarizer having a polarization spindle angle of 22.5 degrees and one pixel, and the repeating unit 915-1 obtains a polarized luminance value of the one pixel. The repeating unit 916-1 includes a polarizer having a polarization spindle angle of 22.5 degrees and one pixel, and the repeating unit 916-1 obtains a polarized luminance value of the one pixel.

The second sensor 9-2 has an imaging unit 90-2 formed with 16 (4×4) repeating units 91-2 to 916-2. The repeating unit 91-2 includes a polarizer having a polarization spindle angle of 67.5 degrees and one pixel, and the repeating unit 91-2 obtains a polarized luminance value of the one pixel. The repeating unit 92-2 includes a polarizer having a polarization spindle angle of 67.5 degrees and one pixel, and the repeating unit 92-2 obtains a polarized luminance value of the one pixel. The repeating unit 93-2 includes a polarizer having a polarization spindle angle of 67.5 degrees and one pixel, and the repeating unit 93-2 obtains a polarized luminance value of the one pixel. The repeating unit 94-2 includes a polarizer having a polarization spindle angle of 67.5 degrees and one pixel, and the repeating unit 94-2 obtains a polarized luminance value of the one pixel.

The repeating unit 95-2 includes one pixel without a polarizer, and the repeating unit 95-2 obtains an unpolarized luminance value of the one pixel. The repeating unit 96-2 includes one pixel without a polarizer, and the repeating unit 96-2 obtains an unpolarized luminance value of the one pixel. The repeating unit 97-2 includes one pixel without a polarizer, and the repeating unit 97-2 obtains an unpolarized luminance value of the one pixel. The repeating unit 98-2 includes one pixel without a polarizer, and the repeating unit 98-2 obtains an unpolarized luminance value of the one pixel.

The repeating unit 99-2 includes one pixel without a polarizer, and the repeating unit 99-2 obtains an unpolarized luminance value of the one pixel. The repeating unit 910-2 includes one pixel without a polarizer, and the repeating unit 910-2 obtains an unpolarized luminance value of the one pixel. The repeating unit 911-2 includes one pixel without a polarizer, and the repeating unit 911-2 obtains an unpolarized luminance value of the one pixel. The repeating unit 912-2 includes one pixel without a polarizer, and the repeating unit 912-2 obtains an unpolarized luminance value of the one pixel.

The repeating unit 913-2 includes a polarizer having a polarization spindle angle of 157.5 degrees and one pixel, and the repeating unit 913-2 obtains a polarized luminance value of the one pixel. The repeating unit 914-2 includes a polarizer having a polarization spindle angle of 157.5 degrees and one pixel, and the repeating unit 914-2 obtains a polarized luminance value of the one pixel. The repeating unit 915-2 includes a polarizer having a polarization spindle angle of 157.5 degrees and one pixel, and the repeating unit 915-2 obtains a polarized luminance value of the one pixel. The repeating unit 916-2 includes a polarizer having a polarization spindle angle of 157.5 degrees and one pixel, and the repeating unit 916-2 obtains a polarized luminance value of the one pixel.

The imaging device 9 has a polarizer in a pixel group. In this manner, polarizers in the same direction can be collectively provided.

Figure 11:
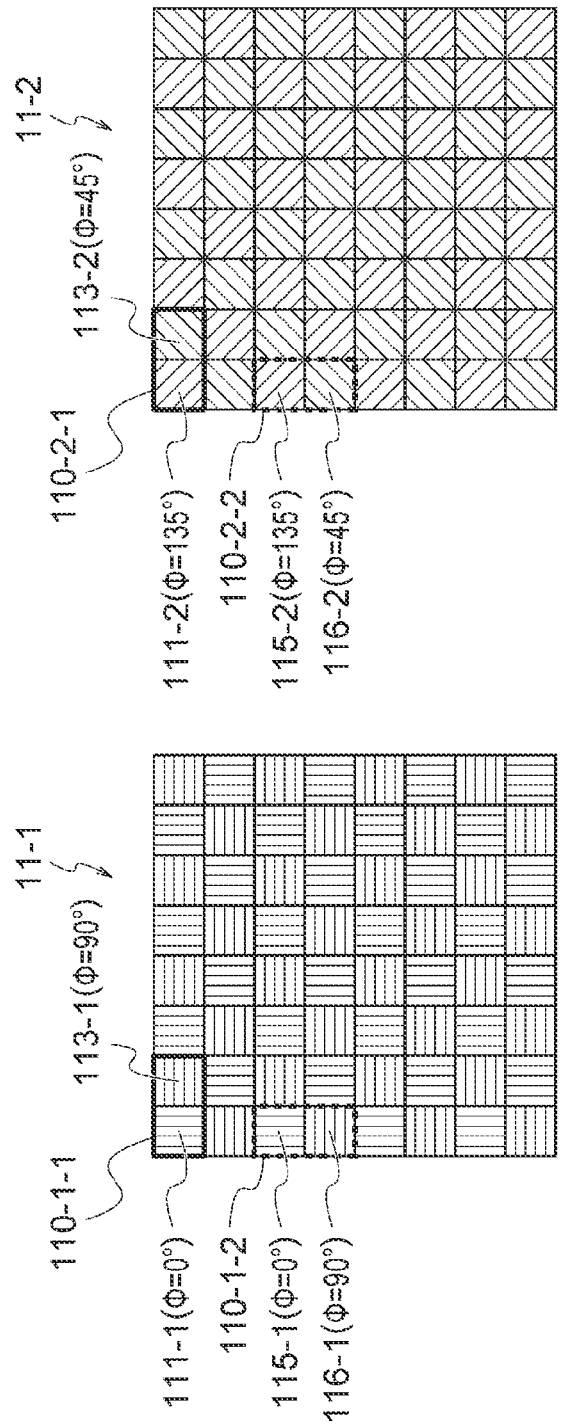
FIG. 11 is a diagram showing example configurations of imaging devices to which the present technology is applied.

FIG. 11 shows an imaging device 11. The imaging device 11 includes a first sensor 11-1 and a second sensor 11-2. That is, the stereo imager included in the imaging device 11 is formed with the first sensor 11-1 and the second sensor 11-2.

The first sensor 11-1 has an imaging unit 110-1-1 formed with two repeating units 111-1 and 113-1 arranged in a horizontal direction (a horizontal direction in FIG. 11). The repeating unit 111-1 includes a polarizer having a polarization spindle angle of 0 degrees and one pixel, and the repeating unit 111-1 obtains a polarized luminance value of the one pixel. The repeating unit 113-1 includes a polarizer having a polarization spindle angle of 90 degrees and one pixel, and the repeating unit 113-1 obtains a polarized luminance value of the one pixel. The first sensor 11-1 also has an imaging unit 110-1-2 formed with two repeating units 115-1 and 116-1 arranged in a vertical direction (a vertical direction in FIG. 11). The repeating unit 115-1 includes a polarizer having a polarization spindle angle of 0 degrees and one pixel, and the repeating unit 115-1 obtains a polarized luminance value of the one pixel. The repeating unit 116-1 includes a polarizer having a polarization spindle angle of 90 degrees and one pixel, and the repeating unit 116-1 obtains a polarized luminance value of the one pixel.

The second sensor 11-2 has an imaging unit 110-2-1 formed with two repeating units 111-2 and 113-2 arranged in a horizontal direction (a horizontal direction in FIG. 11). The repeating unit 111-2 includes a polarizer having a polarization spindle angle of 135 degrees and one pixel, and the repeating unit 111-2 obtains a polarized luminance value of the one pixel. The repeating unit 113-2 includes a polarizer having a polarization spindle angle of 45 degrees and one pixel, and the repeating unit 113-2 obtains a polarized luminance value of the one pixel. The first sensor 11-2 also has an imaging unit 110-2-2 formed with two repeating units 115-2 and 116-2 arranged in a vertical direction (a vertical direction in FIG. 11). The repeating unit 115-2 includes a polarizer having a polarization spindle angle of 135 degrees and one pixel, and the repeating unit 115-2 obtains a polarized luminance value of the one pixel. The repeating unit 116-2 includes a polarizer having a polarization spindle angle of 45 degrees and one pixel, and the repeating unit 116-2 obtains a polarized luminance value of the one pixel.

The imaging device 11 is an example in which the present technology is used for improving not sensitivity but resolution. Since each imager does not acquire three or more pieces of polarization information, it is also possible to achieve a higher resolution than that with a conventional technology.

Figure 12:
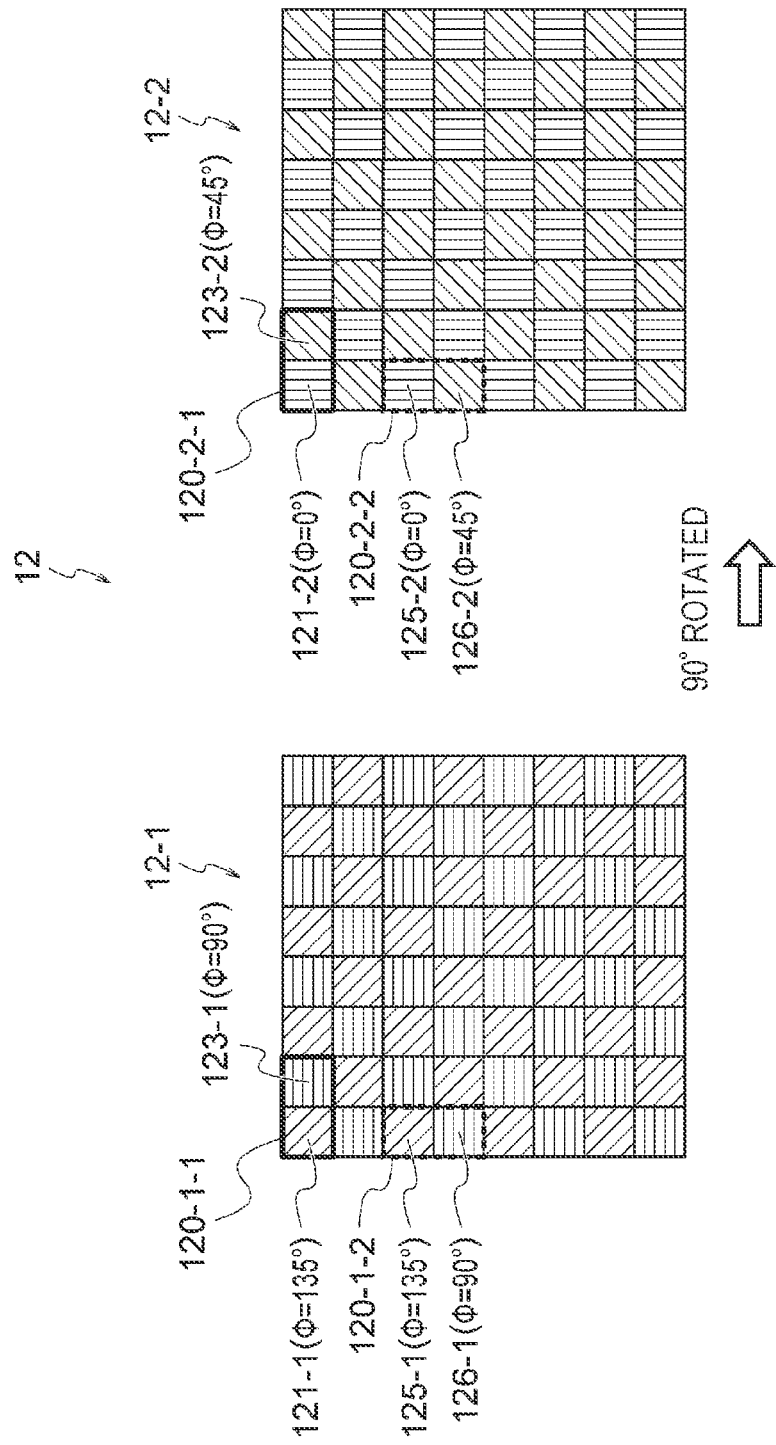
FIG. 12 is a diagram showing example configurations of imaging devices to which the present technology is applied.

FIG. 12 shows an imaging device 12. The imaging device 12 includes a first sensor 12-1 and a second sensor 12-2.

That is, the stereo imager included in the imaging device 12 is formed with the first sensor 12-1 and the second sensor 12-2.

The first sensor 12-1 has an imaging unit 120-1-1 formed with two repeating units 121-1 and 123-1 arranged in a horizontal direction (a horizontal direction in FIG. 12). The repeating unit 121-1 includes a polarizer having a polarization spindle angle of 135 degrees and one pixel, and the repeating unit 121-1 obtains a polarized luminance value of the one pixel. The repeating unit 123-1 includes a polarizer having a polarization spindle angle of 90 degrees and one pixel, and the repeating unit 123-1 obtains a polarized luminance value of the one pixel. The first sensor 12-1 also has an imaging unit 120-1-2 formed with two repeating units 125-1 and 126-1 arranged in a vertical direction (a vertical direction in FIG. 12). The repeating unit 125-1 includes a polarizer having a polarization spindle angle of 135 degrees and one pixel, and the repeating unit 125-1 obtains a polarized luminance value of the one pixel. The repeating unit 126-1 includes a polarizer having a polarization spindle angle of 90 degrees and one pixel, and the repeating unit 126-1 obtains a polarized luminance value of the one pixel.

The second sensor 12-2 has an imaging unit 120-2-1 formed with two repeating units 121-2 and 123-2 arranged in a horizontal direction (a horizontal direction in FIG. 12). The repeating unit 121-2 includes a polarizer having a polarization spindle angle of 0 degrees and one pixel, and the repeating unit 121-2 obtains a polarized luminance value of the one pixel. The repeating unit 123-2 includes a polarizer having a polarization spindle angle of 45 degrees and one pixel, and the repeating unit 123-2 obtains a polarized luminance value of the one pixel. The first sensor 12-2 also has an imaging unit 120-2-2 formed with two repeating units 125-2 and 126-2 arranged in a vertical direction (a vertical direction in FIG. 12). The repeating unit 125-2 includes a polarizer having a polarization spindle angle of 0 degrees and one pixel, and the repeating unit 125-2 obtains a polarized luminance value of the one pixel. The repeating unit 126-2 includes a polarizer having a polarization spindle angle of 45 degrees and one pixel, and the repeating unit 126-2 obtains a polarized luminance value of the one pixel.

As shown in FIG. 12, the imaging device 12 is an example in which one type of sensor is rotated to increase resolution.

Figure 13:
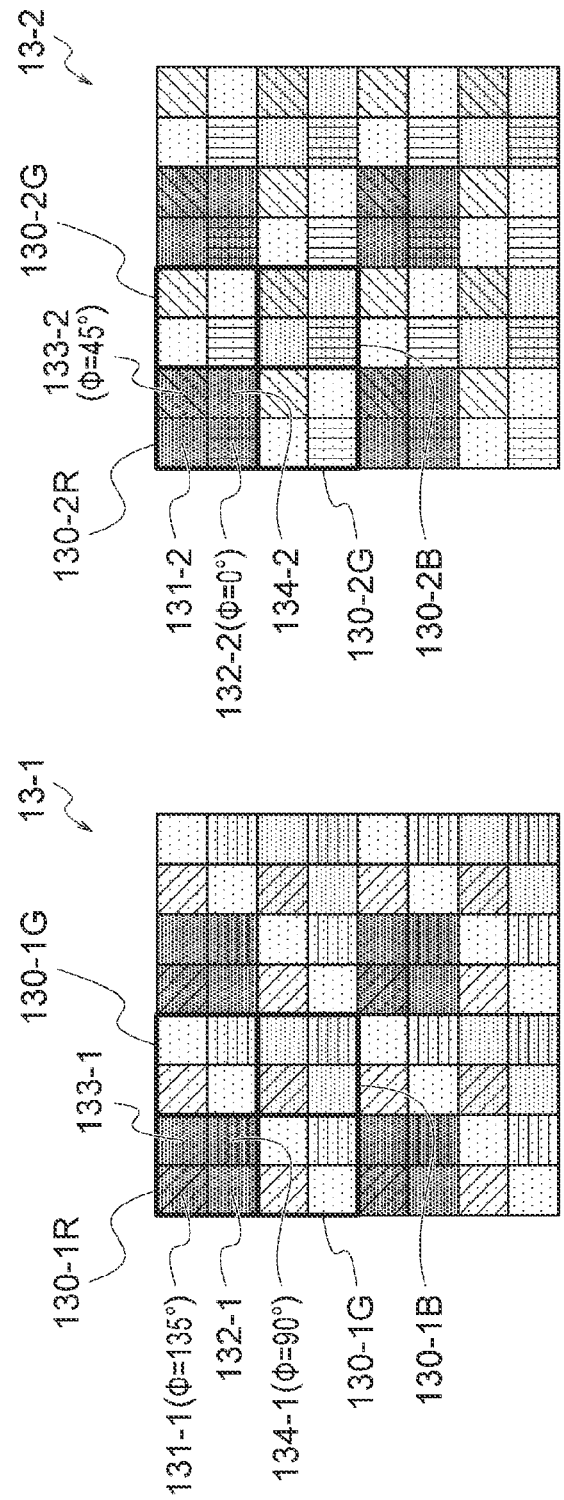
FIG. 13 is a diagram showing example configurations of imaging devices to which the present technology is applied.

FIG. 13 shows an imaging device 13. The imaging device 13 includes a first sensor 13-1 and a second sensor 13-2. That is, the stereo imager included in the imaging device 13 is formed with the first sensor 13-1 and the second sensor 13-2.

The first sensor 13-1 has an imaging unit 130-1R including four repeating units 131-1 to 134-1. The imaging unit 130-1R further includes a color filter for red light. The repeating unit 131-1 includes a polarizer having a polarization spindle angle of 135 degrees and one pixel including a color filter for red light, and the repeating unit 131-1 obtains a color polarized luminance value of the one pixel. The repeating unit 132-1 includes one pixel including a color filter for red light without a polarizer, and the repeating unit 132-1 obtains a color unpolarized luminance value of the one pixel. The repeating unit 133-1 includes one pixel including a color filter for red light without a polarizer, and the repeating unit 133-1 obtains a color unpolarized luminance value of the one pixel. The repeating unit 134-1 includes a polarizer having a polarization spindle angle of 90 degrees and one pixel including a color filter for red light, and the repeating unit 134-1 obtains a color polarized luminance value of the one pixel.

The first sensor 13-1 has an imaging unit 130-1G and an imaging unit 130-1B. The imaging unit 130-1G includes a color filter for green light and is formed with four repeating units. The configurations of the respective repeating units are similar to the configurations of the repeating units of the imaging unit 130-1R described above. Meanwhile, the imaging unit 130-1B includes a color filter for blue light and is formed with four repeating units. The configurations of the respective repeating units are similar to the configurations of the repeating units of the imaging unit 130-1R described above.

The second sensor 13-2 has an imaging unit 130-2R including four repeating units 131-2 to 134-2. The imaging unit 130-2R further includes a color filter for red light. The repeating unit 131-2 includes one pixel including a color filter for red light without a polarizer, and the repeating unit 131-2 obtains a color unpolarized luminance value of the one pixel. The repeating unit 132-2 includes a polarizer having a polarization spindle angle of 0 degrees and one pixel including a color filter for red light, and the repeating unit 132-2 obtains a color polarized luminance value of the one pixel. The repeating unit 133-2 includes a polarizer having a polarization spindle angle of 45 degrees and one pixel including a color filter for red light, and the repeating unit 133-2 obtains a color polarized luminance value of the one pixel. The repeating unit 134-2 includes one pixel including a color filter for red light without a polarizer, and the repeating unit 134-2 obtains a color unpolarized luminance value of the one pixel.

The second sensor 13-2 has an imaging unit 130-2G and an imaging unit 130-2B. The imaging unit 130-2G includes a color filter for green light and is formed with four repeating units. The configurations of the respective repeating units are similar to the configurations of the repeating units of the imaging unit 130-2R described above. Meanwhile, the imaging unit 130-2B includes a color filter for blue light and is formed with four repeating units. The configurations of the respective repeating units are similar to the configurations of the repeating units of the imaging unit 130-2R described above.

The imaging device 13 is an example in which color filters are provided in the sensors (imagers), and the colors of the color filters are changed for sets of polarization information. As described above, the imaging device 13 can obtain a color image at the same time as a distance image.

Figure 14:
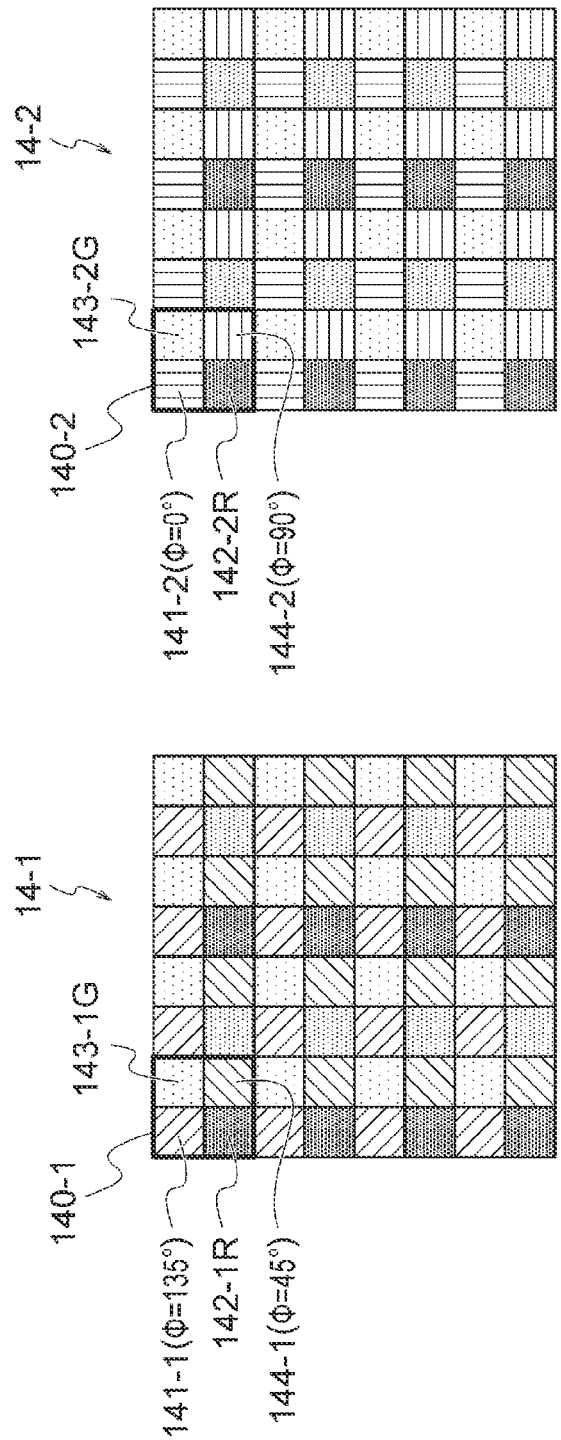
FIG. 14 is a diagram showing example configurations of imaging devices to which the present technology is applied.

FIG. 14 shows an imaging device 14. The imaging device 14 includes a first sensor 14-1 and a second sensor 14-2. That is, the stereo imager included in the imaging device 14 is formed with the first sensor 14-1 and the second sensor 14-2.

The first sensor 14-1 has an imaging unit 140-1 formed with four repeating units 141-1, 142-1R, 143-1G, and 144-1. The repeating unit 141-1 includes a polarizer having a polarization spindle angle of 135 degrees and one pixel, and the repeating unit 141-1 obtains a polarized luminance value of the one pixel. The repeating unit 142-1R includes one pixel including a color filter for red light without a polarizer, and the repeating unit 142-1R obtains a color unpolarized luminance value of the one pixel. The repeating unit 143-1G includes one pixel including a color filter for green light without a polarizer, and the repeating unit 143-1G obtains a color unpolarized luminance value of the one pixel. The repeating unit 144-1 includes a polarizer having a polarization spindle angle of 45 degrees and one pixel, and the repeating unit 144-1 obtains a polarized luminance value of the one pixel.

The second sensor 14-2 has an imaging unit 140-2 formed with four repeating units 141-1, 142-2R, 143-2G, and 144-2. The repeating unit 141-2 includes a polarizer having a polarization spindle angle of 0 degrees and one pixel, and the repeating unit 141-2 obtains a polarized luminance value of the one pixel. The repeating unit 142-2R includes one pixel including a color filter for red light without a polarizer, and the repeating unit 142-2R obtains a color unpolarized luminance value of the one pixel. The repeating unit 143-2G includes one pixel including a color filter for green light without a polarizer, and the repeating unit 143-2G obtains a color unpolarized luminance value of the one pixel. The repeating unit 144-2 includes a polarizer having a polarization spindle angle of 90 degrees and one pixel, and the repeating unit 144-2 obtains a polarized luminance value of the one pixel.

The imaging device 14 is an example in which color filters are provided in the sensors (imagers), and the color filters that separate colors are provided only in the non-polarized pixels. It is also possible to obtain a color image at the same time as a distance image.

Figure 15:
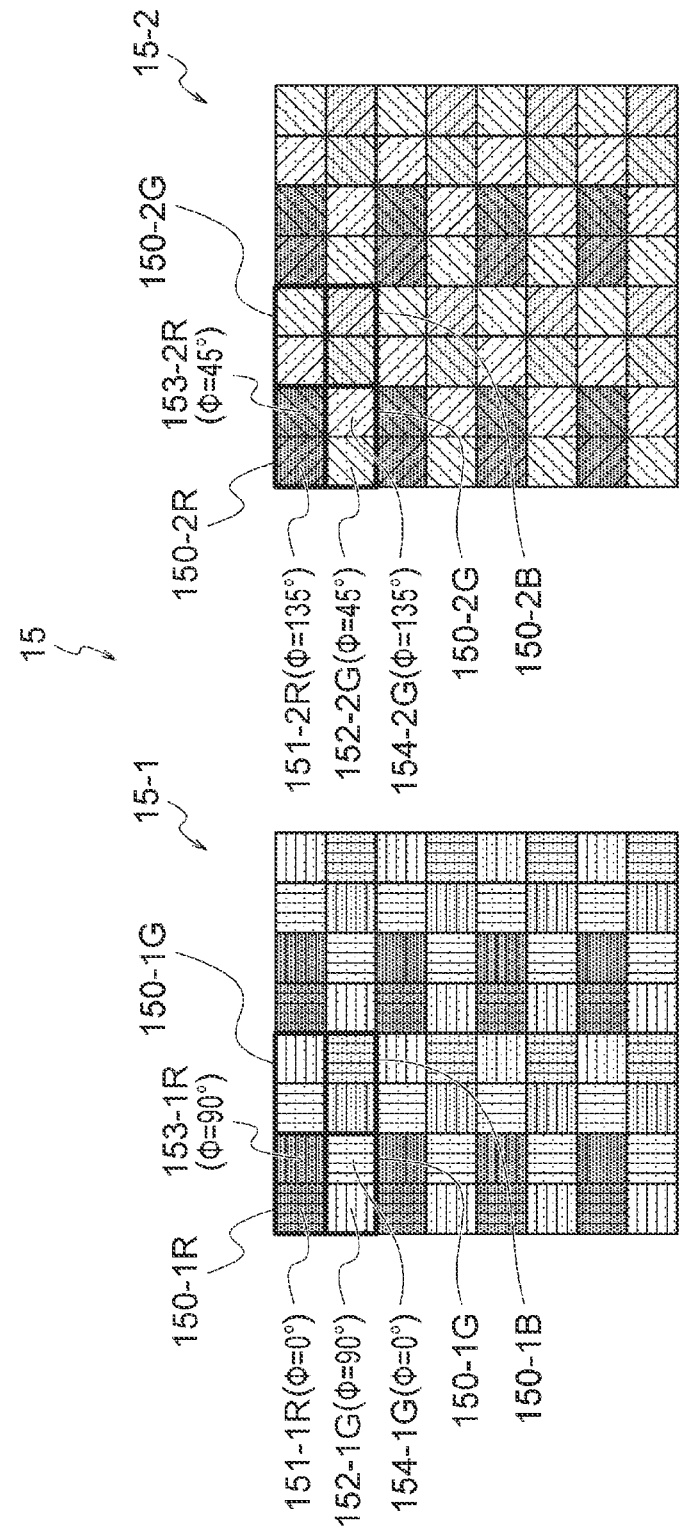
FIG. 15 is a diagram showing example configurations of imaging devices to which the present technology is applied.

FIG. 15 shows an imaging device 15. The imaging device 15 includes a first sensor 15-1 and a second sensor 15-2. That is, the stereo imager included in the imaging device 14 is formed with the first sensor 15-1 and the second sensor 15-2.

The first sensor 15-1 has an imaging unit 150-1R formed with two repeating units 151-1R and 153-1R arranged in a horizontal direction (a horizontal direction in FIG. 15). The imaging unit 150-1R includes a color filter for red light. The repeating unit 151-1R includes a polarizer having a polarization spindle angle of 0 degrees and one pixel including a color filter for red light, and the repeating unit 151-1R obtains a color polarized luminance value of the one pixel. The repeating unit 153-1R includes a polarizer having a polarization spindle angle of 90 degrees and one pixel including a color filter for red light, and the repeating unit 153-1R obtains a color polarized luminance value of the one pixel. The first sensor 15-1 has an imaging unit 150-1G formed with two repeating units 152-1G and 154-1G arranged in a horizontal direction (a horizontal direction in FIG. 15), on the lower side of the imaging unit 150-1R. The imaging unit 150-1G includes a color filter for green light. The repeating unit 152-1G includes a polarizer having a polarization spindle angle of 90 degrees and one pixel including a color filter for green light, and the repeating unit 152-1G obtains a color polarized luminance value of the one pixel. The repeating unit 154-1G includes a polarizer having a polarization spindle angle of 0 degrees and one pixel including a color filter for green light, and the repeating unit 154-1G obtains a color polarized luminance value of the one pixel. The first sensor 15-1 also has an imaging unit 150-1G formed with two repeating units arranged in a horizontal direction (a horizontal direction in FIG. 15), on the right side of the imaging unit 150-1R. The imaging unit 150-1G on the right side of the imaging unit 150-1R is formed by rotating 180 degrees the imaging unit 150-1G on the lower side of the imaging unit 150-1R. The first sensor 15-1 further has an imaging unit 150-1B formed with two repeating units arranged in a horizontal direction (a horizontal direction in FIG. 15), on the lower right side of the imaging unit 150-1R. The imaging unit 150-1B includes a color filter for blue color. The configurations of the repeating units of the imaging unit 150-1B are similar to the configurations of the repeating units of the imaging unit 150-1G.

The first sensor 15-2 has an imaging unit 150-2R formed with two repeating units 152-1R and 153-2R arranged in a horizontal direction (a horizontal direction in FIG. 15). The imaging unit 150-2R includes a color filter for red light. The repeating unit 151-2R includes a polarizer having a polarization spindle angle of 135 degrees and one pixel including a color filter for red light, and the repeating unit 151-2R obtains a color polarized luminance value of the one pixel. The repeating unit 153-2R includes a polarizer having a polarization spindle angle of 45 degrees and one pixel including a color filter for red light, and the repeating unit 153-2R obtains a color polarized luminance value of the one pixel. The first sensor 15-2 has an imaging unit 150-2G formed with two repeating units 152-2G and 154-2G arranged in a horizontal direction (a horizontal direction in FIG. 15), on the lower side of the imaging unit 150-2R. The imaging unit 150-2G includes a color filter for green light. The repeating unit 152-2G includes a polarizer having a polarization spindle angle of 45 degrees and one pixel including a color filter for green light, and the repeating unit 152-2G obtains a color polarized luminance value of the one pixel. The repeating unit 154-2G includes a polarizer having a polarization spindle angle of 135 degrees and one pixel including a color filter for green light, and the repeating unit 154-2G obtains a color polarized luminance value of the one pixel. The second sensor 15-2 also has an imaging unit 150-2G formed with two repeating units arranged in a horizontal direction (a horizontal direction in FIG. 15), on the right side of the imaging unit 150-2R. The imaging unit 150-2G on the right side of the imaging unit 150-2R is formed by rotating 180 degrees the imaging unit 150-2G on the lower side of the imaging unit 150-2R. The second sensor 15-2 further has an imaging unit 150-2B formed with two repeating units arranged in a horizontal direction (a horizontal direction in FIG. 15), on the lower right side of the imaging unit 150-2R. The imaging unit 150-2B includes a color filter for blue color. The configurations of the repeating units of the imaging unit 150-2B are similar to the configurations of the repeating units of the imaging unit 150-2G.

The imaging device 15 has the same purpose (concept) as that of the imaging device 13, but is an example in which all the sensors (imagers) are polarized pixels. However, color filters may be provided in any of the imagers 1 to 12.

FIG. 16 shows a sensor 16-1 forming an imaging device. In the sensor 16-1, on-chip lenses 161, polarizers 167-1 and 167-2 formed in an insulating film 162, a light-blocking material 163, a semiconductor substrate 164 in which photodiodes 166 are formed, and a transistor/wiring layer 165 are arranged in this order from the light incident side. The polarizers 167-1 and 167-2 and the on-chip lenses 161 are disposed on the light receiving side of the photodiodes 166. The polarizers 167-1 and 167-2 can be formed with thin metal wires, for example.

FIG. 17 shows a sensor 17-1 forming an imaging device. In the sensor 17-1, on-chip lenses 171, color filters (color filters for W light, a color filter for R light, and a color filter for B light), polarizers 177-1 and 177-2 formed in an insulating film 172, a light-blocking material 173, a semiconductor substrate 174 in which photodiodes 176W for W light, a photodiode 176R for R light, and a photodiode for B light are formed, and a transistor/wiring layer 175 are arranged in this order from the light incident side. The sensor 17-1 shown in FIG. 17 is an example in which color filters that separate colors only for non-polarized pixels are provided, like the sensor 14-1 or 14-2 shown in FIG. 14. It is also possible to provide color filters that separate colors for polarized pixels. In that case, the color filters for W light may be replaced with color filters that separate a desired color from the others.

FIG. 18 is a diagram showing an example of an imaging mode in which an imaging device of the first embodiment according to the present technology is used in an above described manner. As shown in FIG. 18, an imaging device of the first embodiment according to the present technology includes a camera 1000-1 and a camera 1000-2. The camera 1000-1 has a sensor 2000-1 including an imager that is a light receiving region, and the camera 1000-2 has a sensor 2000-2 including an imager is a light receiving region. In the imaging mode shown in FIG. 18, images of an object 300 are captured with the camera 1000-1 and the camera 1000-2, which are the two sensors (the sensor 2000-1 and the sensor 2000-2).

FIG. 19 is a flowchart showing a flow in a process for obtaining a high-precision distance image from images captured as shown in FIG. 18, for example.

First, the process is started in step S0. In step S1-1, an image of a first sensor (the first sensor 1-1 in FIG. 1, for example; the same applies in the description below) is acquired. In step S1-2, an image of a second sensor (the first sensor 1-2 in FIG. 1, for example; the same applies in the description below) is acquired.

Next, in step S2-1, a luminance image of the first sensor is created. In step S2-3, a luminance image of each polarization direction of the first sensor is created. In step S2-2, a luminance image of the second sensor is then created. In step S2-4, a luminance image of each polarization direction of the second sensor is created. For example, luminance images in which a unit image obtained by the imaging units shown in FIGS. 1 to 15 is regarded as one pixel, and luminance images of only the respective polarized pixels are created.

In step S3, matching is performed on the luminance images obtained in steps S2-1 and S2-2. For example, matching is performed on the luminance image in which the unit image obtained from the first sensor is regarded as one pixel and the luminance image in which the unit image obtained from the second sensor is regarded as one pixel. Matching is to associate the pixels that capture the same site with each other. Matching methods are roughly classified into the two methods: feature-based matching and region-based matching, but there are also matching methods that combine both. Any of those methods can be used. Note that, as for the matching method, it is possible to refer to the non-patent document (The 25th Signal Processing Symposium, Nov. 24-26, 2010 (in Nara), "Examination of High-Precision Image Matching Methods"), for example.

In step S4-1, a distance image is created. In step S4-2, polarization information (Imax, Imin, and φ) is calculated from each polarization luminance image of the corresponding position. In step s5, azimuth angle and zenith angle images are created. In step S6, a high-precision distance image can be created.

Specifically, the above matching information is used, and a distance image is created from a luminance image in which a unit image obtained from the first sensor is regarded as one pixel, and a luminance image in which a unit image obtained from the second sensor is regarded as one pixel. If the distance (called the baseline length) between the first imager and the second imager is known, the distance in the Depth direction (the direction perpendicular to the two sensors) can be calculated from the number of pixels shifted in each imager according to the matching information. The polarization information is then calculated. Imax, Imin, and φ can be obtained from the brightness of each polarized light that captures the same site, according to the model shown in FIGS. 20A and 20B, which will be described later.

The normal vector is not clear only from the above Imax, Imin, and φ, due to indefiniteness. However, when the distance image created as described above is used, it is possible to determine whether the distance becomes longer or shorter at a time of movement in a certain direction from the point of interest, as shown in FIGS. 21A, 21B, 21C and 21D described later. Accordingly, the angle between the azimuth angle α and the zenith angle θ can be determined. By recalculating the distance image using the obtained normal information, it is possible to create a high-precision distance image as described later.

FIGS. 20A, 20B, 21A, 21B, 21C, 21D, 22, 23 and 24 are diagrams for explaining that an imaging device of the first embodiment according to the present technology is used to generate normal information and obtain a distance image (3D information) in the above described manner.

Figure 20B:
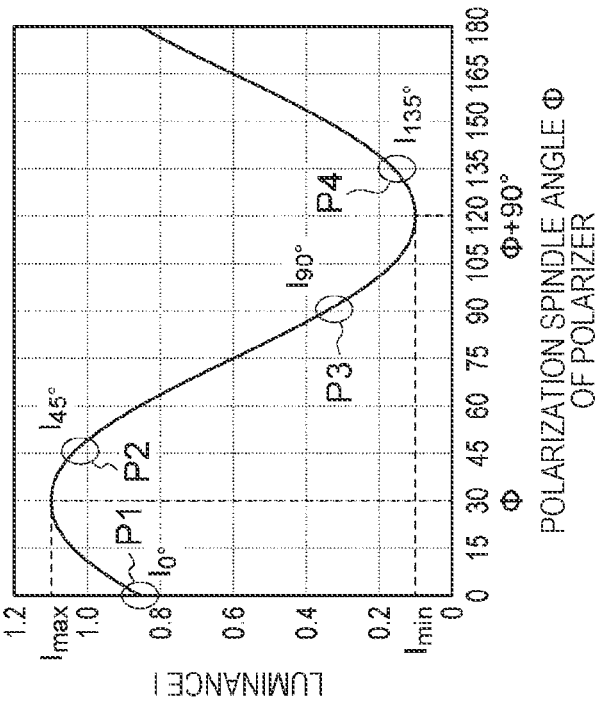
FIGS. 20A and 20B are diagrams for explaining that an imaging device according to the present technology is used to generate normal information and obtain a distance image.
Figure 20A:
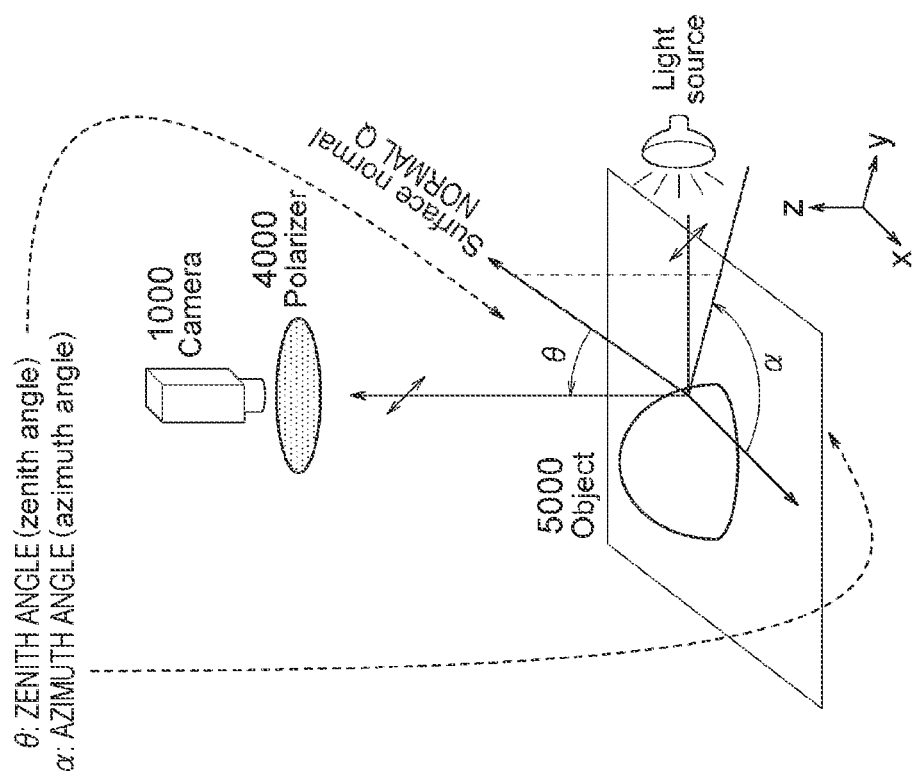

FIG. 20A shows the relationship among the normal Q, the zenith angle θ, and the azimuth angle α in the positional relationship among a camera 1000, a polarizer 4000, and an object 5000. In the graph shown in FIG. 20B, the abscissa axis indicates the polarization spindle angle φ of the polarizer, and the ordinate axis indicates luminance I. The graph in FIG. 20B shows that the luminances P1 to P4 of light that has passed through four kinds of polarizers with polarization spindle angles of 0 degrees, 45 degrees, 90 degrees, and 135 degrees form one sine function curve. Imax, Imin, and φ can be calculated from this sine function curve.

Figures 21A, 21B, 21C, 21D:
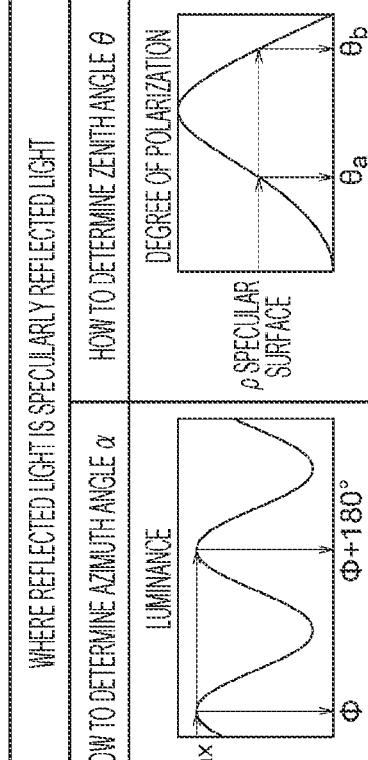
FIGS. 21A, 21B, 21C, and 21D are diagrams for explaining that an imaging device according to the present technology is used to generate normal information and obtain a distance image.

FIGS. 21A and 21B show how the azimuth angle α and the zenith angle θ are determined in a case where reflected light is specularly reflected light. Further, FIGS. 21C and 21D show how the azimuth angle α and the zenith angle θ are determined in a case where the reflected light is diffusely reflected light. In the graphs in FIGS. 21B and 21D, the ordinate axis indicates the degree of polarization p, which can be calculated according to (Imax−Imin)/(Imax+Imin).

Figure 22:
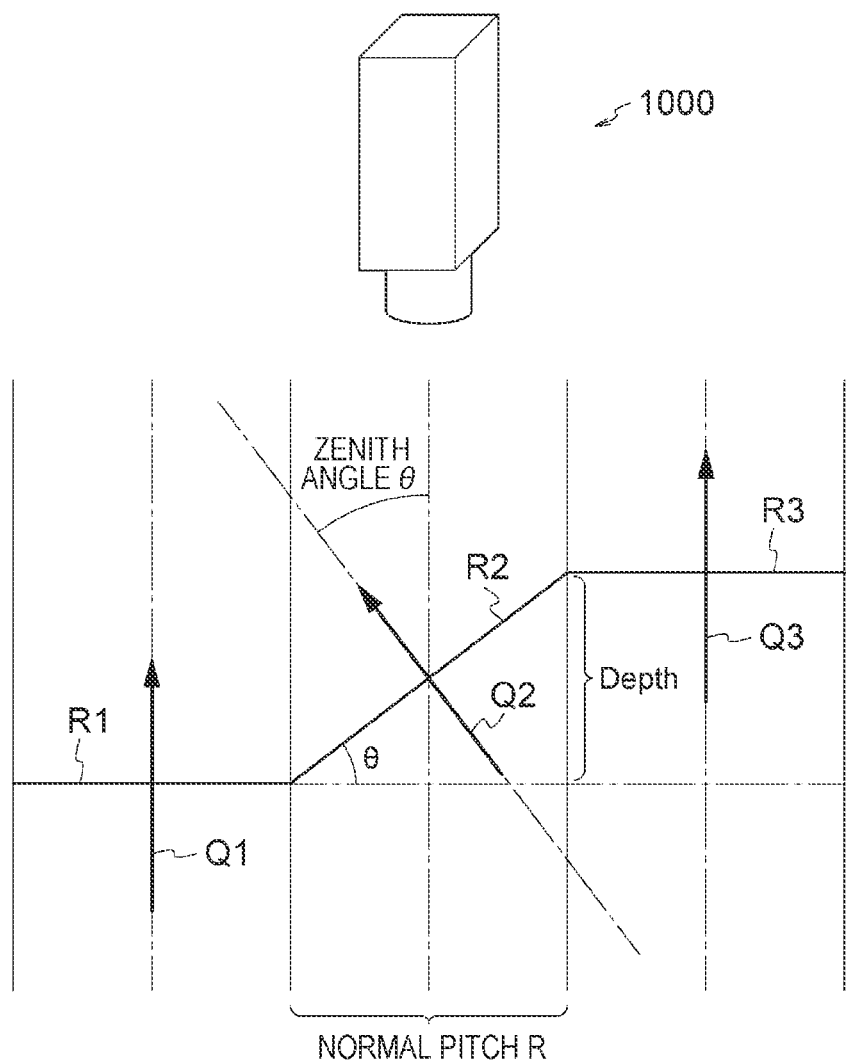
FIG. 22 is a diagram for explaining that an imaging device according to the present technology is used to generate normal information and obtain a distance image.

FIG. 22 shows the normal vector Q1 on a surface R1 of an object, the normal vector Q2 on a surface R2 of the object, and the normal vector Q3 on a surface R3 of the object. In FIG. 22, it is assumed that the object distance corresponding to the normal vector Q1 is known in advance from distance (absolute distance) information. The normal pitch R is then determined by "(pixel pitch×object distance)/focal length", and the depth (the surface unevenness of the object, or 3D information) can be determined by "depth=normal pitch·tan (zenith angle θ)".

3. Second Embodiment (Example 2 of an Imaging Device)

An imaging device of a second embodiment (Example 2 of an imaging device) according to the present technology is an imaging device that includes a stereo imager. The stereo imager includes a first sensor, a second sensor, and a third sensor. The first sensor has a first imaging unit formed with a plurality of repeating units, the second sensor has a second imaging unit formed with a plurality of repeating units, and the third sensor has a third imaging unit formed with a plurality of repeating units. The first imaging unit includes a polarizer having at least one kind of polarization spindle angle, the second imaging unit includes a polarizer having at least one kind of polarization spindle angle, and the third imaging unit includes a polarizer having at least one kind of polarization spindle angle. A first unit image obtained by the first imaging unit, a second unit image obtained by the second imaging unit, and a third unit image obtained by the third imaging unit are combined, so that information about polarization in at least three directions is acquired, and normal information is generated. That is, the imaging device of the second embodiment according to the present technology acquires information about polarization in at least three directions and generates normal information, using three sensors. In the imaging device of the second embodiment according to the present technology, to generate normal information, it is only required to acquire information about polarization in at least three directions. Therefore, the information about polarization may be information about polarization in three directions, information about polarization in four directions, or information about polarization in five or more directions.

With the imaging device of the second embodiment according to the present technology, it is possible to further increase the accuracy of distance information. More specifically, with the imaging device of the second embodiment according to the present technology, pixels polarized in at least three directions are not provided in the respective sensors of a plurality of (three) sensors. Accordingly, polarized pixels can be reduced, and non-polarized pixels can be provided instead. Thus, sensitivity can be increased. Further, instead of non-polarized pixels, pixels polarized in a desired direction may be provided in each sensor of the plurality of (three) sensors. Thus, the resolution of normal information can be increased. As the resolution of normal information becomes higher, the accuracy of the distance direction (the accuracy of 3D information) can be increased.

In the imaging device of the second embodiment according to the present technology, the polarizer having at least one kind of polarization spindle angle of the first imaging unit, the polarizer having at least one kind of polarization spindle angle of the second imaging unit, and the polarizer having at least one kind of polarization spindle angle of the third imaging unit preferably differ from one another in polarization spindle angle. The second imaging unit preferably includes no polarizer having at least one kind of polarization spindle angle of the first imaging unit and no polarizer having at least one kind of polarization spindle angle of the third imaging unit, and the third imaging unit preferably includes no polarizer having at least one kind of polarization spindle angle of the first imaging unit and no polarizer having at least one kind of polarization spindle angle of the second imaging unit.

In the imaging device of the second embodiment according to the present technology, the first unit image, the second unit image, and the third unit image are preferably reconstructed on the basis of the stereo correspondence relationship.

In the imaging device of the second embodiment according to the present technology, the first imaging unit preferably includes a polarizer having two or less kinds of polarization spindle angles, the second imaging unit preferably includes a polarizer having two or less kinds of polarization spindle angles, and the third imaging unit preferably includes a polarizer having two or less kinds of polarization spindle angles.

In the imaging device of the second embodiment according to the present technology, the first imaging unit preferably includes a polarizer having two kinds of polarization spindle angles, and the two kinds of polarization spindle angles are preferably orthogonal to each other in the first imaging unit. The second imaging unit preferably includes a polarizer having two kinds of polarization spindle angles, and the two kinds of polarization spindle angles are preferably orthogonal to each other in the second imaging unit. The third imaging unit preferably includes a polarizer having two kinds of polarization spindle angles, and the two kinds of polarization spindle angles are preferably orthogonal to each other in the third imaging unit.

In the imaging device of the second embodiment according to the present technology, the first imaging unit preferably includes at least a polarizer having a polarization spindle angle of 22.5 degrees and a polarizer having a polarization spindle angle of 112.5 degrees, while the second imaging unit preferably includes a polarizer having a polarization spindle angle of 67.5 degrees and a polarizer having a polarization spindle angle of 157.5 degrees. Also, in the imaging device of the second embodiment according to the present technology, the first imaging unit preferably includes at least a polarizer having a polarization spindle angle of 22.5 degrees and a polarizer having a polarization spindle angle of 112.5 degrees, while the third imaging unit preferably includes a polarizer having a polarization spindle angle of 67.5 degrees and a polarizer having a polarization spindle angle of 157.5 degrees. Further, in the imaging device of the second embodiment according to the present technology, the second imaging unit preferably includes at least a polarizer having a polarization spindle angle of 22.5 degrees and a polarizer having a polarization spindle angle of 112.5 degrees, while the third imaging unit preferably includes a polarizer having a polarization spindle angle of 67.5 degrees and a polarizer having a polarization spindle angle of 157.5 degrees.

In the imaging device of the second embodiment according to the present technology, the first imaging unit preferably includes a polarizer having one kind of polarization spindle angle, the second imaging unit preferably includes a polarizer having one kind of polarization spindle angle, and the third imaging unit preferably includes a polarizer having one kind of polarization spindle angle. The difference among the polarization spindle angle of the polarizer included in the first imaging unit, the polarization spindle angle of the polarizer included in the second imaging unit, and the polarization spindle angle of the polarizer included in the third imaging unit is preferably not smaller than five degrees and not greater than 85 degrees.

In the imaging device of the second embodiment according to the present technology, the first imaging unit preferably has repeating units including polarizers and repeating units not including polarizers, the second imaging unit preferably has repeating units including polarizers and repeating units not including polarizers, and the third imaging unit preferably has repeating units including polarizers and repeating units not including polarizers. The ratio between the repeating units including polarizers and the repeating units not including polarizers in the first imaging unit, the ratio between the repeating units including polarizers and the repeating units not including polarizers in the second imaging unit, and the ratio between the repeating units including polarizers and the repeating units not including polarizers in the third imaging unit are preferably substantially the same.

In the imaging device of the second embodiment according to the present technology, the first imaging unit preferably has repeating units including polarizers and repeating units not including polarizers, the second imaging unit preferably has repeating units including polarizers and repeating units not including polarizers, and the third imaging unit preferably has repeating units including polarizers and repeating units not including polarizers. The layout pattern of the repeating units including polarizers and the repeating units not including polarizers in the first imaging unit, the layout pattern of the repeating units including polarizers and the repeating units not including polarizers in the second imaging unit, and the layout pattern of the repeating units including polarizers and the repeating units not including polarizers in the third imaging unit are preferably substantially the same.

Figure 10:
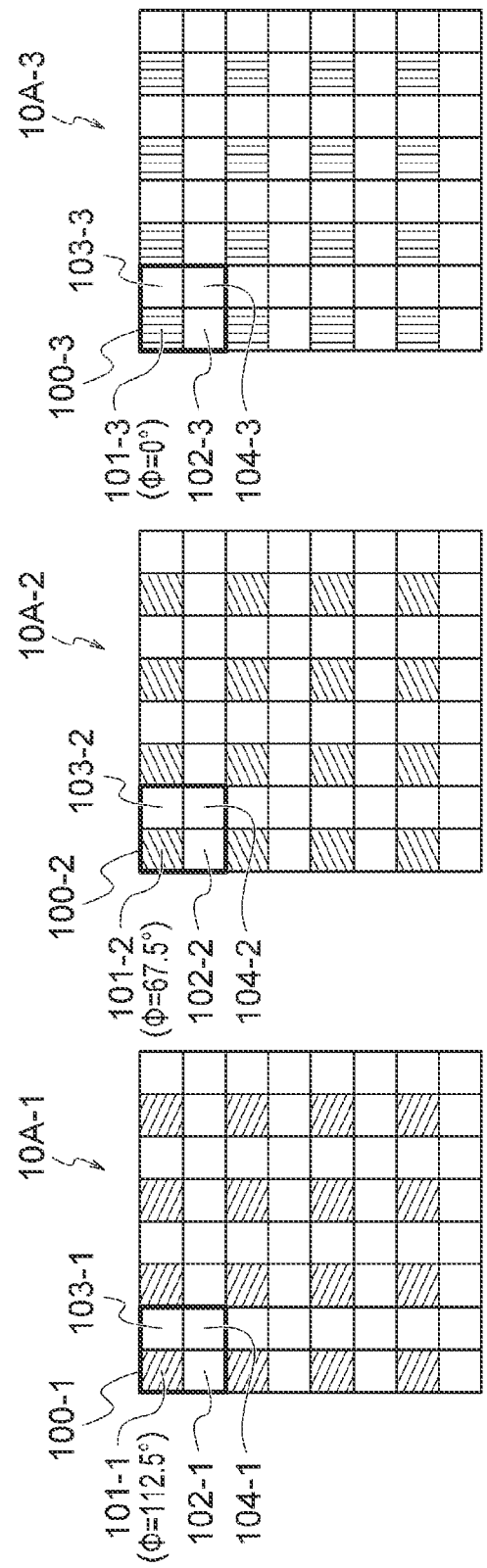
FIG. 10 is a diagram showing example configurations of imaging devices to which the present technology is applied.

In the description below, an imaging device of the second embodiment according to the present technology is explained in greater detail, with reference to FIG. 10. FIG. 10 is a diagram showing an example configuration of an imaging device of the second embodiment according to the present technology.

FIG. 10 shows an imaging device 10A. The imaging device 10A includes a first sensor 10A-1, a second sensor 10A-2, and a third sensor 10A-3. That is, the stereo imager included in the imaging device 10A is formed with the first sensor 10A-1, the second sensor 10A-2, and the third sensor 10A-3.

The first sensor 10A-1 has an imaging unit 100-1 formed with four repeating units 101-1 to 104-1. The repeating unit 101-1 includes a polarizer having a polarization spindle angle of 112.5 degrees and one pixel, and the repeating unit 101-1 obtains a polarized luminance value of the one pixel. The repeating unit 102-1 includes one pixel without a polarizer, and the repeating unit 102-1 obtains an unpolarized luminance value of the one pixel. The repeating unit 103-1 includes one pixel without a polarizer, and the repeating unit 103-1 obtains an unpolarized luminance value of the one pixel. The repeating unit 104-1 includes one pixel without polarization, and the repeating unit 104-1 obtains an unpolarized luminance value of the one pixel.

The second sensor 10A-2 has an imaging unit 100-2 formed with four repeating units 101-2 to 104-2. The repeating unit 101-2 includes a polarizer having a polarization spindle angle of 67.5 degrees and one pixel, and the repeating unit 101-2 obtains a polarized luminance value of the one pixel. The repeating unit 102-2 includes one pixel without a polarizer, and the repeating unit 102-2 obtains an unpolarized luminance value of the one pixel. The repeating unit 103-2 includes one pixel without a polarizer, and the repeating unit 103-2 obtains an unpolarized luminance value of the one pixel. The repeating unit 104-2 includes one pixel without polarization, and the repeating unit 104-2 obtains an unpolarized luminance value of the one pixel.

The third sensor 10A-3 has an imaging unit 100-3 formed with four repeating units 101-3 to 104-3. The repeating unit 101-3 includes a polarizer having a polarization spindle angle of 0 degrees and one pixel, and the repeating unit 101-3 obtains a polarized luminance value of the one pixel. The repeating unit 102-3 includes one pixel without a polarizer, and the repeating unit 102-3 obtains an unpolarized luminance value of the one pixel. The repeating unit 103-3 includes one pixel without a polarizer, and the repeating unit 103-3 obtains an unpolarized luminance value of the one pixel. The repeating unit 104-3 includes one pixel without polarization, and the repeating unit 104-3 obtains an unpolarized luminance value of the one pixel.

The contents described in the chapter <2. First Embodiment (Example 1 of an Imaging Device)>concerning imaging devices of the first embodiment according to the present technology, including the contents illustrated in FIGS. 16, 17, 18, 19, 20A, 20B, 21A, 21B, 21C, 21D and 22, can be applied to the imaging device of the second embodiment according to the present technology, without any change.

4. Third Embodiment (an Example of an Electronic Apparatus)

An electronic apparatus of a third embodiment according to the present technology is an electronic apparatus in which an imaging device according to the present technology is mounted. A first aspect of an imaging device according to the present technology includes a stereo imager. The stereo imager includes a plurality of sensors. Each of the plurality of sensors has an imaging unit formed with a plurality of repeating units, and the imaging unit includes a polarizer having at least one kind of polarization spindle angle. At least two unit images obtained by a plurality of the imaging units are combined, to obtain information about polarization in at least three directions and generate normal information. Further, a second aspect of an imaging device according to the present technology is an imaging device that includes a stereo imager. The stereo imager includes a first sensor and a second sensor. The first sensor has a first imaging unit formed with a plurality of repeating units, and the second sensor has a second imaging unit formed with a plurality of repeating units. The first imaging unit includes a polarizer having at least one kind of polarization spindle angle, and the second imaging unit includes a polarizer having at least one kind of polarization spindle angle. A first unit image obtained by the first imaging unit and a second unit image obtained by the second imaging unit are combined, so that information about polarization in at least three directions is acquired, and normal information is generated. Note that the sensors included in the stereo imager may be two sensors as described above, or may be three sensors, or may be four or more sensors.

For example, an electronic apparatus of the third embodiment according to the present technology is an electronic apparatus in which an imaging device of one embodiment among the imaging devices of the first and second embodiments according to the present technology is mounted.

Figure 23:
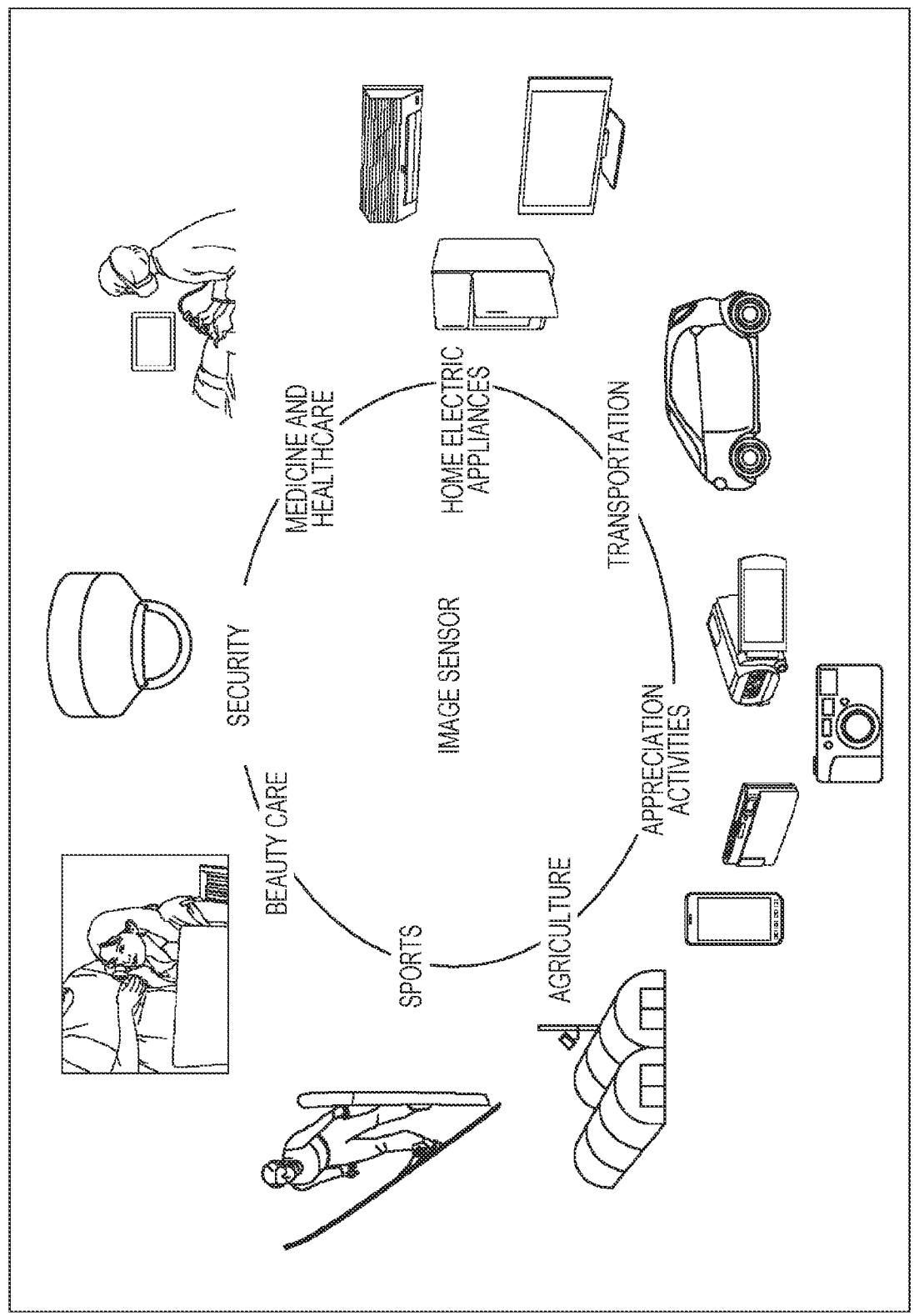
FIG. 23 is a diagram showing examples of use of imaging devices of first and second embodiments to which the present technology is applied.

5. Examples of Use of Imaging Devices to which the Present Technology is Applied FIG. 23 is a diagram showing examples of use of imaging devices of the first and second embodiments according to the present technology as image sensors.

Imaging devices of the first and second embodiments described above can be used in various cases where light such as visible light, infrared light, ultraviolet light, or an X-ray is sensed, as described below, for example. That is, as shown in FIG. 23, imaging devices of the first or second embodiment can be used in apparatuses (such as the electronic apparatus of the sixth embodiment described above, for example) that are used in the appreciation activity field where images are taken and are used in appreciation activities, the field of transportation, the field of home electric appliances, the fields of medicine and healthcare, the field of security, the field of beauty care, the field of sports, the field of agriculture, and the like, for example.

Specifically, in the appreciation activity field, an imaging device of the first or second embodiment can be used in an apparatus for capturing images to be used in appreciation activities, such as a digital camera, a smartphone, or a portable telephone with a camera function, for example.

In the field of transportation, an imaging device of the first or second embodiment can be used in an apparatus for transportation use, such as a vehicle-mounted sensor designed to capture images of the front, the back, the surroundings, the inside, and the like of an automobile, to perform safe driving such as an automatic stop and recognize the driver's condition or the like, a surveillance camera for monitoring running vehicles and roads, and a ranging sensor or the like for measuring distances between vehicles or the like, for example.

In the field of home electric appliances, an imaging device of the first or second embodiment can be used in an apparatus to be used as home electric appliances, such as a television set, a refrigerator, or an air conditioner, to capture images of gestures of users and operate the apparatus in accordance with the gestures, for example.

In the fields of medicine and healthcare, an imaging device of the first or second embodiment can be used in an apparatus for medical use or healthcare use, such as an endoscope or an apparatus for receiving infrared light for angiography, for example.

In the field of security, an imaging device of the first or second embodiment can be used in an apparatus for security use, such as a surveillance camera for crime prevention or a camera for personal authentication, for example.

In the field of beauty care, an imaging device of the first or second embodiment can be used in an apparatus for beauty care use, such as a skin measurement apparatus designed to capture images of the skin or a microscope for capturing images of the scalp, for example.

In the field of sports, an imaging device of the first or second embodiment can be used in an apparatus for sporting use, such as an action camera or a wearable camera for sports or the like, for example.

In the field of agriculture, an imaging device of the first or second embodiment can be used in an apparatus for agricultural use, such as a camera for monitoring conditions of fields and crops, for example.

Figure 24:
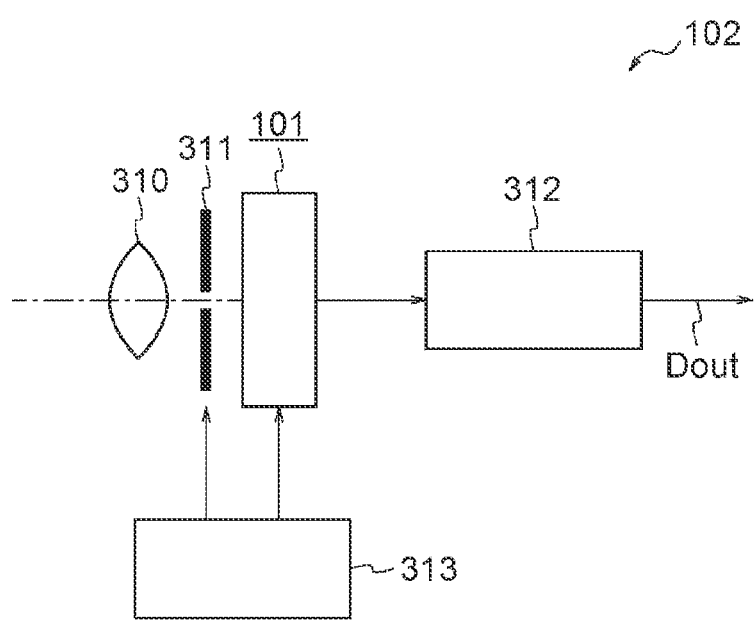
FIG. 24 is a functional block diagram of an example of an electronic apparatus according to a third embodiment to which the present technology is applied.

Next, examples of use of imaging devices of the first and second embodiments according to the present technology are specifically described. For example, an imaging device of the first or second embodiment described above can be used as an imaging device 101 in an electronic apparatus of any type having an imaging function, such as a camera system like a digital still camera or a video camera, or a portable telephone having an imaging function. FIG. 24 shows a schematic configuration of an electronic apparatus 102 (a camera) as an example. This electronic apparatus 102 is a video camera capable of capturing a still image or a moving image, for example, and includes the imaging device 101, an optical system (an optical lens) 310, a shutter device 311, a drive unit 313 that drives the imaging device 101 and the shutter device 311, and a signal processing unit 312.

The optical system 310 guides image light (incident light) from the object to a pixel unit 101a of the imaging device 101. This optical system 310 may be formed with a plurality of optical lenses. The shutter device 311 controls the light irradiation period and the light blocking period for the imaging device 101. The drive unit 313 controls transfer operations of the imaging device 101 and shutter operations of the shutter device 311. The signal processing unit 312 performs various kinds of signal processing on a signal output from the solid-state imaging device 101. A video signal Dout subjected to the signal processing is stored into a storage medium such as a memory, or is output to a monitor or the like.

6. Example Application to an Endoscopic Surgery System

The present technology can be applied to various products. For example, the technology (the present technology) according to the present disclosure may be applied to an endoscopic surgery system.

Figure 25:
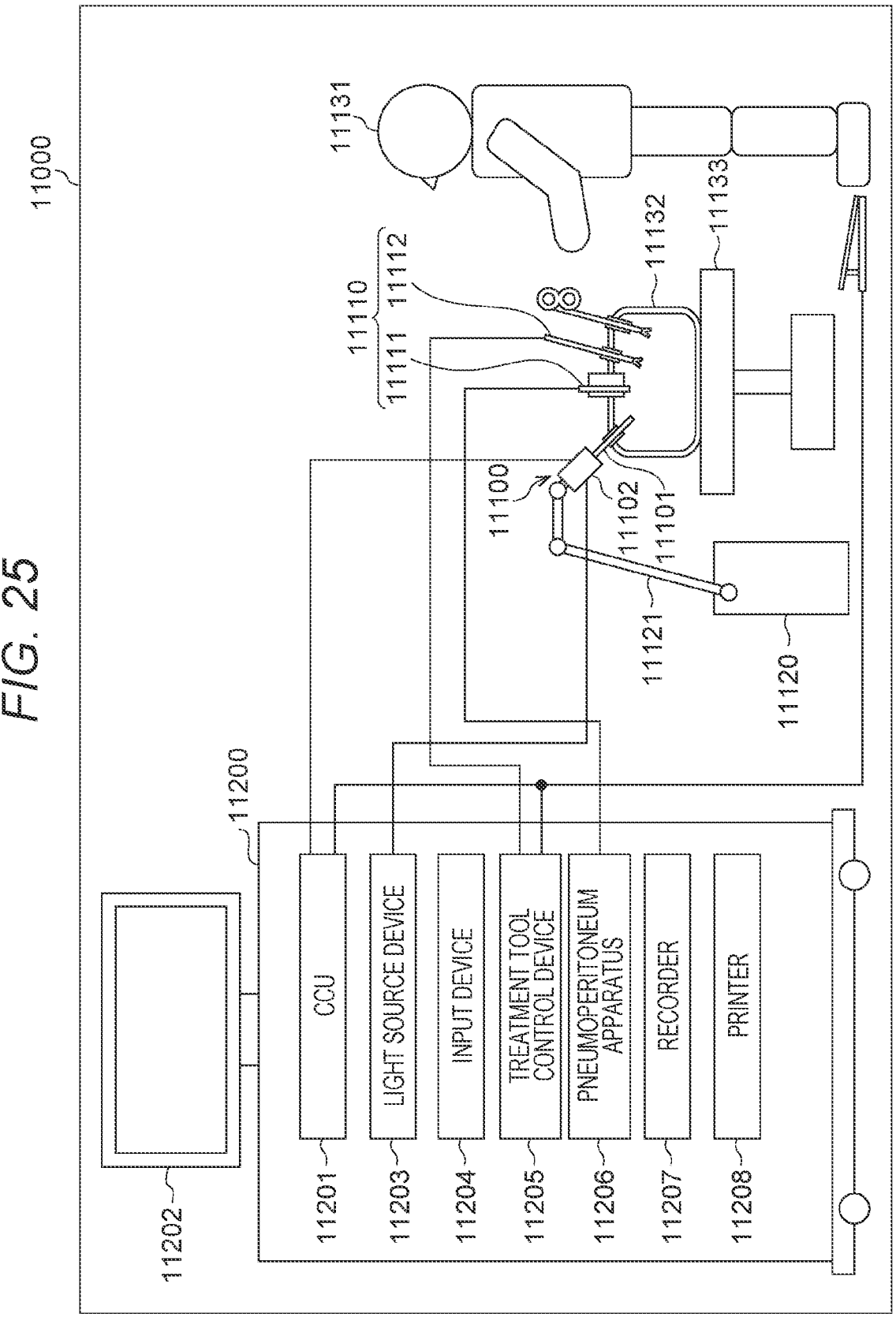
FIG. 25 is a diagram schematically showing an example configuration of an endoscopic surgery system.

FIG. 25 is a diagram schematically showing an example configuration of an endoscopic surgery system to which the technology (the present technology) according to the present disclosure may be applied.

FIG. 25 shows a situation where a surgeon (a physician) 11131 is performing surgery on a patient 11132 on a patient bed 11133, using an endoscopic surgery system 11000. As shown in the drawing, the endoscopic surgery system 11000 includes an endoscope 11100, other surgical tools 11110 such as a pneumoperitoneum tube 11111 and an energy treatment tool 11112, a support arm device 11120 that supports the endoscope 11100, and a cart 11200 on which various kinds of devices for endoscopic surgery are mounted.

The endoscope 11100 includes a lens barrel 11101 that has a region of a predetermined length from the top end to be inserted into a body cavity of the patient 11132, and a camera head 11102 connected to the base end of the lens barrel 11101. In the example shown in the drawing, the endoscope 11100 is designed as a so-called rigid scope having a rigid lens barrel 11101. However, the endoscope 11100 may be designed as a so-called flexible scope having a flexible lens barrel.

At the top end of the lens barrel 11101, an opening into which an objective lens is inserted is provided. A light source device 11203 is connected to the endoscope 11100, and the light generated by the light source device 11203 is guided to the top end of the lens barrel by a light guide extending inside the lens barrel 11101, and is emitted toward the current observation target in the body cavity of the patient 11132 via the objective lens. Note that the endoscope 11100 may be a forward-viewing endoscope, an oblique-viewing endoscope, or a side-viewing endoscope.

An optical system and imaging elements are provided inside the camera head 11102, and reflected light (observation light) from the current observation target is converged on the imaging elements by the optical system. The observation light is photoelectrically converted by the imaging elements, and an electrical signal corresponding to the observation light, or an image signal corresponding to the observation image, is generated. The image signal is transmitted as RAW data to a camera control unit (CCU) 11201.

The CCU 11201 is formed with a central processing unit (CPU), a graphics processing unit (GPU), or the like, and collectively controls operations of the endoscope 11100 and a display device 11202. Further, the CCU 11201 receives an image signal from the camera head 11102, and subjects the image signal to various kinds of image processing, such as a development process (a demosaicing process), for example, to display an image based on the image signal.

Under the control of the CCU 11201, the display device 11202 displays an image based on the image signal subjected to the image processing by the CCU 11201.

The light source device 11203 is formed with a light source such as a light emitting diode (LED), for example, and supplies the endoscope 11100 with illuminating light for imaging the surgical site or the like.

An input device 11204 is an input interface to the endoscopic surgery system 11000. The user can input various kinds of information and instructions to the endoscopic surgery system 11000 via the input device 11204. For example, the user inputs an instruction or the like to change imaging conditions (such as the type of illuminating light, the magnification, and the focal length) for the endoscope 11100.

A treatment tool control device 11205 controls driving of the energy treatment tool 11112 for tissue cauterization, incision, blood vessel sealing, or the like. A pneumoperitoneum device 11206 injects a gas into a body cavity of the patient 11132 via the pneumoperitoneum tube 11111 to inflate the body cavity, for the purpose of securing the field of view of the endoscope 11100 and the working space of the surgeon. A recorder 11207 is a device capable of recording various kinds of information about the surgery. A printer 11208 is a device capable of printing various kinds of information relating to the surgery in various formats such as text, images, graphics, and the like.

Note that the light source device 11203 that supplies the endoscope 11100 with the illuminating light for imaging the surgical site can be formed with an LED, a laser light source, or a white light source that is a combination of an LED and a laser light source, for example. In a case where a white light source is formed with a combination of RGB laser light sources, the output intensity and the output timing of each color (each wavelength) can be controlled with high precision. Accordingly, the white balance of an image captured by the light source device 11203 can be adjusted. Alternatively, in this case, laser light from each of the RGB laser light sources may be emitted onto the current observation target in a time-division manner, and driving of the imaging elements of the camera head 11102 may be controlled in synchronization with the timing of the light emission. Thus, images corresponding to the respective RGB colors can be captured in a time-division manner. According to the method, a color image can be obtained without any color filter provided in the imaging elements.

Further, the driving of the light source device 11203 may also be controlled so that the intensity of light to be output is changed at predetermined time intervals. The driving of the imaging elements of the camera head 11102 is controlled in synchronism with the timing of the change in the intensity of the light, and images are acquired in a time-division manner and are then combined. Thus, a high dynamic range image with no black portions and no white spots can be generated.

Further, the light source device 11203 may also be designed to be capable of supplying light of a predetermined wavelength band compatible with special light observation. In special light observation, light of a narrower band than the illuminating light (or white light) at the time of normal observation is emitted, with the wavelength dependence of light absorption in body tissue being taken advantage of, for example. As a result, so-called narrow band light observation (narrow band imaging) is performed to image predetermined tissue such as a blood vessel in a mucosal surface layer or the like, with high contrast. Alternatively, in the special light observation, fluorescence observation for obtaining an image with fluorescence generated through emission of excitation light may be performed. In fluorescence observation, excitation light is emitted to body tissue so that the fluorescence from the body tissue can be observed (autofluorescence observation). Alternatively, a reagent such as indocyanine green (ICG) is locally injected into body tissue, and excitation light corresponding to the fluorescence wavelength of the reagent is emitted to the body tissue so that a fluorescent image can be obtained, for example. The light source device 11203 can be designed to be capable of supplying narrow band light and/or excitation light compatible with such special light observation.

Figure 26:
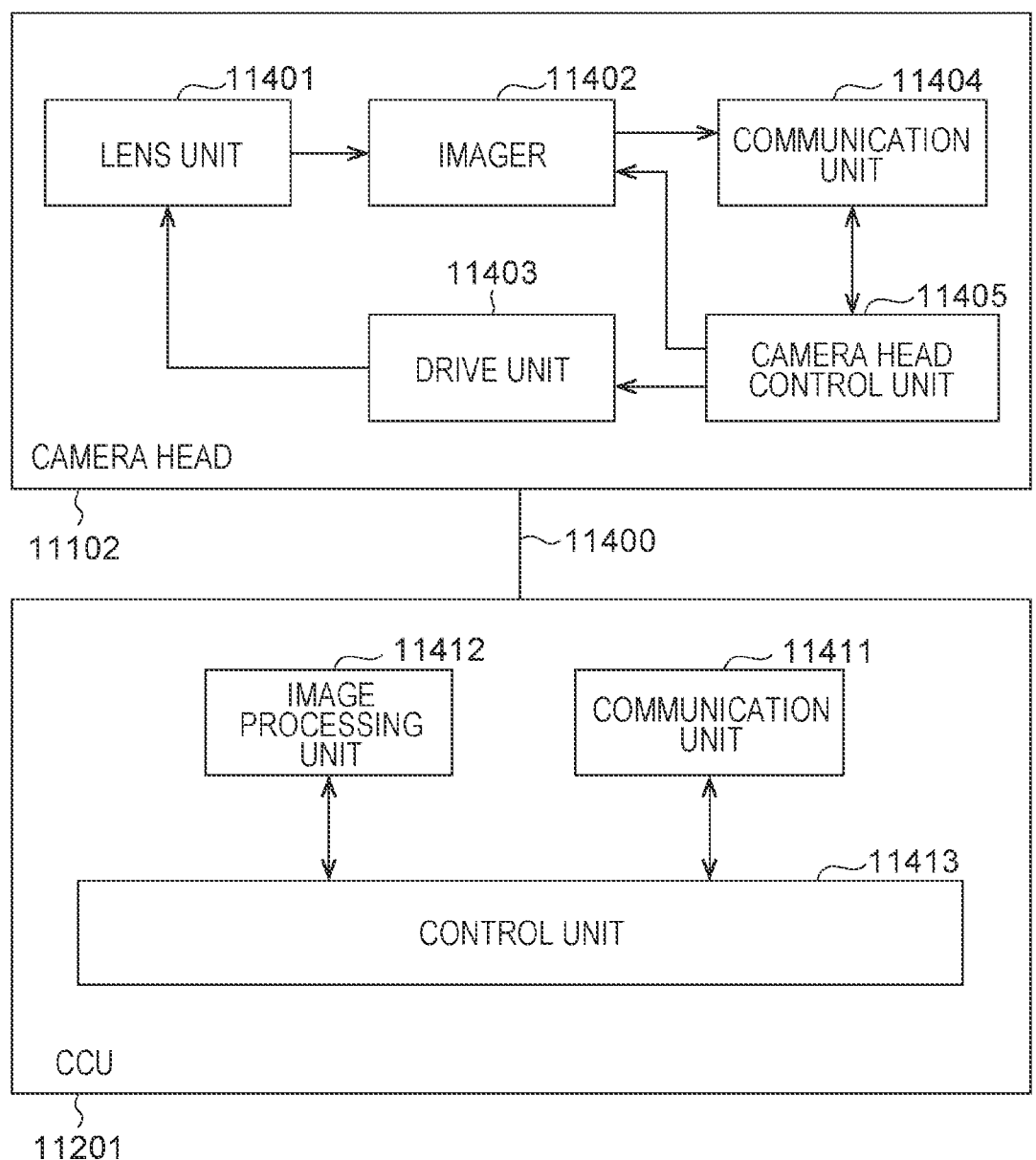
FIG. 26 is a block diagram showing an example of the functional configurations of a camera head and a CCU.

FIG. 26 is a block diagram showing an example of the functional configurations of the camera head 11102 and the CCU 11201 shown in FIG. 25.

The camera head 11102 includes a lens unit 11401, an imager 11402, a drive unit 11403, a communication unit 11404, and a camera head control unit 11405. The CCU 11201 includes a communication unit 11411, an image processing unit 11412, and a control unit 11413. The camera head 11102 and the CCU 11201 are communicably connected to each other by a transmission cable 11400.

The lens unit 11401 is an optical system provided at the connecting portion with the lens barrel 11101. Observation light captured from the top end of the lens barrel 11101 is guided to the camera head 11102, and enters the lens unit 11401. The lens unit 11401 is formed with a combination of a plurality of lenses including a zoom lens and a focus lens.

The imager 11402 is formed with imaging elements. The imager 11402 may be formed with one imaging element (a so-called single-plate type), or may be formed with a plurality of imaging elements (a so-called multiple-plate type). In a case where the imager 11402 is of a multiple-plate type, for example, image signals corresponding to the respective RGB colors may be generated by the respective imaging elements, and be then combined to obtain a color image. Alternatively, the imager 11402 may be designed to include a pair of imaging elements for acquiring right-eye and left-eye image signals compatible with three-dimensional (3D) display. As the 3D display is conducted, the surgeon 11131 can grasp more accurately the depth of the body tissue at the surgical site. Note that, in a case where the imager 11402 is of a multiple-plate type, a plurality of lens units 11401 is provided for the respective imaging elements.

Further, the imager 11402 is not necessarily provided in the camera head 11102. For example, the imager 11402 may be provided immediately behind the objective lens in the lens barrel 11101.

The drive unit 11403 is formed with an actuator, and, under the control of the camera head control unit 11405, moves the zoom lens and the focus lens of the lens unit 11401 by a predetermined distance along the optical axis. With this arrangement, the magnification and the focal point of the image captured by the imager 11402 can be adjusted as appropriate.

The communication unit 11404 is formed with a communication device for transmitting and receiving various kinds of information to and from the CCU 11201. The communication unit 11404 transmits the image signal obtained as RAW data from the imager 11402 to the CCU 11201 via the transmission cable 11400.

The communication unit 11404 also receives a control signal for controlling the driving of the camera head 11102 from the CCU 11201, and supplies the control signal to the camera head control unit 11405. The control signal includes information about imaging conditions, such as information for specifying the frame rate of captured images, information for specifying the exposure value at the time of imaging, and/or information for specifying the magnification and the focal point of captured images, for example.

Note that the above imaging conditions such as the frame rate, the exposure value, the magnification, and the focal point may be appropriately specified by the user, or may be automatically set by the control unit 11413 of the CCU 11201 on the basis of an acquired image signal. In the latter case, the endoscope 11100 has a so-called auto-exposure (AE) function, an auto-focus (AF) function, and an auto-white-balance (AWB) function.

The camera head control unit 11405 controls the driving of the camera head 11102, on the basis of a control signal received from the CCU 11201 via the communication unit 11404.

The communication unit 11411 is formed with a communication device for transmitting and receiving various kinds of information to and from the camera head 11102. The communication unit 11411 receives an image signal transmitted from the camera head 11102 via the transmission cable 11400.

Further, the communication unit 11411 also transmits a control signal for controlling the driving of the camera head 11102, to the camera head 11102. The image signal and the control signal can be transmitted through electrical communication, optical communication, or the like.

The image processing unit 11412 performs various kinds of image processing on an image signal that is RAW data transmitted from the camera head 11102.

The control unit 11413 performs various kinds of control relating to display of an image of the surgical portion or the like captured by the endoscope 11100, and a captured image obtained through imaging of the surgical site or the like. For example, the control unit 11413 generates a control signal for controlling the driving of the camera head 11102.

Further, the control unit 11413 also causes the display device 11202 to display a captured image showing the surgical site or the like, on the basis of the image signal subjected to the image processing by the image processing unit 11412. In doing so, the control unit 11413 may recognize the respective objects shown in the captured image, using various image recognition techniques. For example, the control unit 11413 can detect the shape, the color, and the like of the edges of an object shown in the captured image, to recognize the surgical tool such as forceps, a specific body site, bleeding, the mist at the time of use of the energy treatment tool 11112, and the like. When causing the display device 11202 to display the captured image, the control unit 11413 may cause the display device 11202 to superimpose various kinds of surgery aid information on the image of the surgical site on the display, using the recognition result. As the surgery aid information is superimposed and displayed, and thus, is presented to the surgeon 11131, it becomes possible to reduce the burden on the surgeon 11131, and enable the surgeon 11131 to proceed with the surgery in a reliable manner.

The transmission cable 11400 connecting the camera head 11102 and the CCU 11201 is an electrical signal cable compatible with electric signal communication, an optical fiber compatible with optical communication, or a composite cable thereof.

Here, in the example shown in the drawing, communication is performed in a wired manner using the transmission cable 11400. However, communication between the camera head 11102 and the CCU 11201 may be performed in a wireless manner.

An example of an endoscopic surgery system to which the technique according to the present disclosure can be applied has been described above. The technology according to the present disclosure may be applied to the endoscope 11100, the imager 11402 of the camera head 11102, and the like in the configuration described above, for example. Specifically, the solid-state imaging device 111 of the present disclosure can be applied to the imager 10402. By applying the technique according to the present disclosure to the endoscope 11100, (the imager 11402) of the camera head 11102, and the like, it is possible to improve the yield and reduce the manufacturing costs.

Although the endoscopic surgery system has been described as an example herein, the technology according to the present disclosure may be applied to a microscopic surgery system or the like, for example.

7. Example Applications to Mobile Structures

The technology (the present technology) according to the present disclosure can be applied to various products. For example, the technology according to the present disclosure may be embodied as a device mounted on any type of mobile structure, such as an automobile, an electrical vehicle, a hybrid electrical vehicle, a motorcycle, a bicycle, a personal mobility device, an airplane, a drone, a vessel, or a robot.

Figure 27:
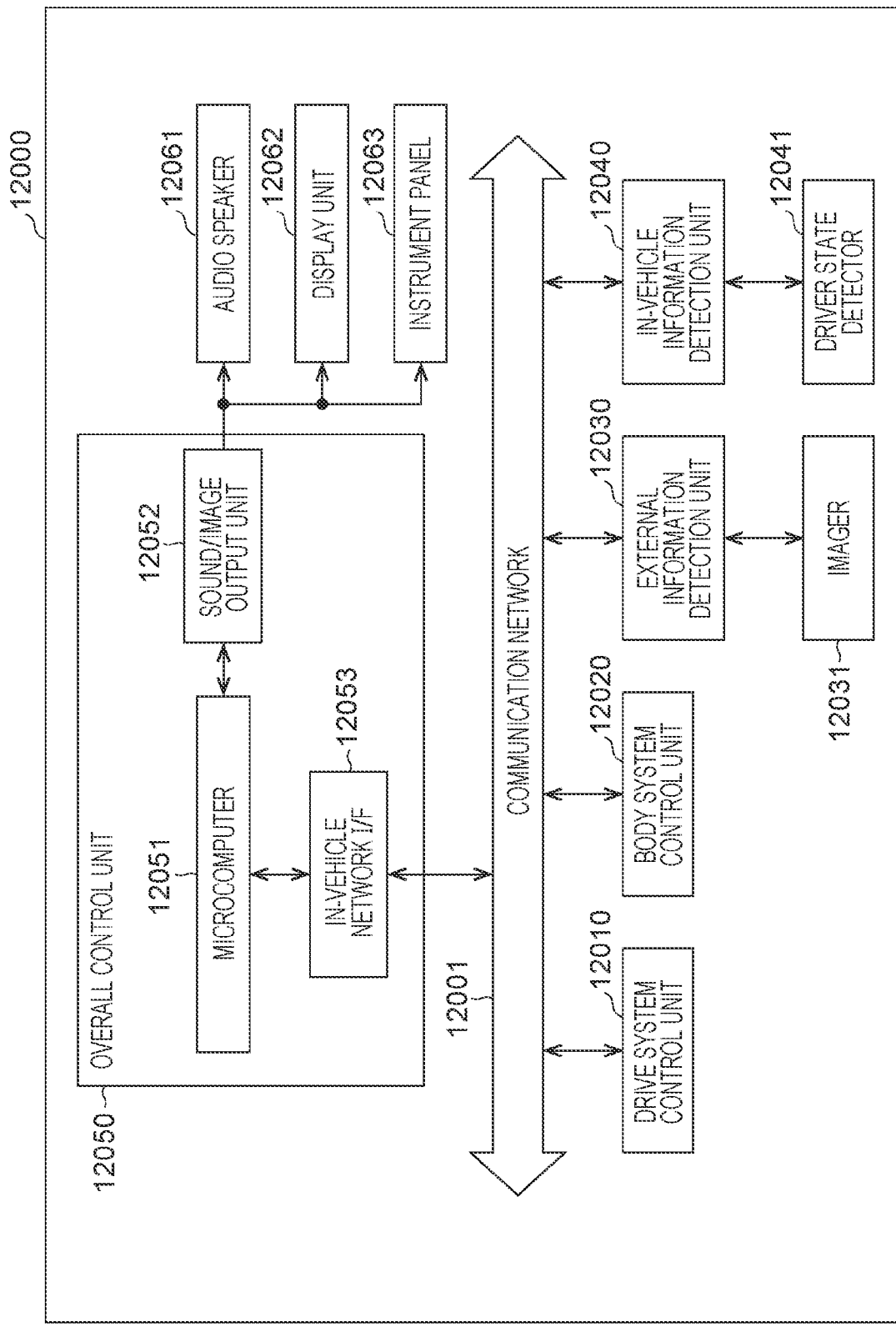
FIG. 27 is a block diagram schematically showing an example configuration of a vehicle control system.

FIG. 27 is a block diagram schematically showing an example configuration of a vehicle control system that is an example of a mobile structure control system to which the technology according to the present disclosure may be applied.

A vehicle control system 12000 includes a plurality of electronic control units connected via a communication network 12001. In the example shown in FIG. 27, the vehicle control system 12000 includes a drive system control unit 12010, a body system control unit 12020, an external information detection unit 12030, an in-vehicle information detection unit 12040, and an overall control unit 12050. Further, a microcomputer 12051, a sound/image output unit 12052, and an in-vehicle network interface (I/F) 12053 are shown as the functional components of the overall control unit 12050.

The drive system control unit 12010 controls operations of the devices related to the drive system of the vehicle according to various programs. For example, the drive system control unit 12010 functions as control devices such as a driving force generation device for generating a driving force of the vehicle such as an internal combustion engine or a driving motor, a driving force transmission mechanism for transmitting the driving force to the wheels, a steering mechanism for adjusting the steering angle of the vehicle, and a braking device for generating a braking force of the vehicle.

The body system control unit 12020 controls operations of the various devices mounted on the vehicle body according to various programs. For example, the body system control unit 12020 functions as a keyless entry system, a smart key system, a power window device, or a control device for various lamps such as a headlamp, a backup lamp, a brake lamp, a turn signal lamp, a fog lamp, or the like. In this case, the body system control unit 12020 can receive radio waves transmitted from a portable device that substitutes for a key, or signals from various switches. The body system control unit 12020 receives inputs of these radio waves or signals, and controls the door lock device, the power window device, the lamps, and the like of the vehicle.

The external information detection unit 12030 detects information outside the vehicle equipped with the vehicle control system 12000. For example, an imager 12031 is connected to the external information detection unit 12030. The external information detection unit 12030 causes the imager 12031 to capture an image of the outside of the vehicle, and receives the captured image. On the basis of the received image, the external information detection unit 12030 may perform an object detection process for detecting a person, a vehicle, an obstacle, a sign, characters on the road surface, or the like, or perform a distance detection process.

The imager 12031 is an optical sensor that receives light, and outputs an electrical signal corresponding to the amount of received light. The imager 12031 can output an electrical signal as an image, or output an electrical signal as distance measurement information. Further, the light to be received by the imager 12031 may be visible light, or may be invisible light such as infrared rays.

The in-vehicle information detection unit 12040 detects information about the inside of the vehicle. For example, a driver state detector 12041 that detects the state of the driver is connected to the in-vehicle information detection unit 12040. The driver state detector 12041 includes a camera that captures an image of the driver, for example, and, on the basis of detected information input from the driver state detector 12041, the in-vehicle information detection unit 12040 may calculate the degree of fatigue or the degree of concentration of the driver, or determine whether or not the driver is dozing off.

On the basis of the external/internal information acquired by the external information detection unit 12030 or the in-vehicle information detection unit 12040, the microcomputer 12051 can calculate the control target value of the driving force generation device, the steering mechanism, or the braking device, and output a control command to the drive system control unit 12010. For example, the microcomputer 12051 can perform cooperative control to achieve the functions of an advanced driver assistance system (ADAS), including vehicle collision avoidance or impact mitigation, follow-up running based on the distance between vehicles, vehicle velocity maintenance running, vehicle collision warning, vehicle lane deviation warning, or the like.

Further, the microcomputer 12051 can also perform cooperative control to conduct automatic driving or the like for autonomously running not depending on the operation of the driver, by controlling the driving force generation device, the steering mechanism, the braking device, or the like on the basis of information about the surroundings of the vehicle, the information having being acquired by the external information detection unit 12030 or the in-vehicle information detection unit 12040.

The microcomputer 12051 can also output a control command to the body system control unit 12020, on the basis of the external information acquired by the external information detection unit 12030. For example, the microcomputer 12051 controls the headlamp in accordance with the position of the leading vehicle or the oncoming vehicle detected by the external information detection unit 12030, and performs cooperative control to achieve an anti-glare effect by switching from a high beam to a low beam, or the like.

The sound/image output unit 12052 transmits an audio output signal and/or an image output signal to an output device that is capable of visually or audibly notifying the passenger(s) of the vehicle or the outside of the vehicle of information. In the example shown in FIG. 27, an audio speaker 12061, a display unit 12062, and an instrument panel 12063 are shown as output devices. The display unit 12062 may include an on-board display and/or a head-up display, for example.

Figure 28:
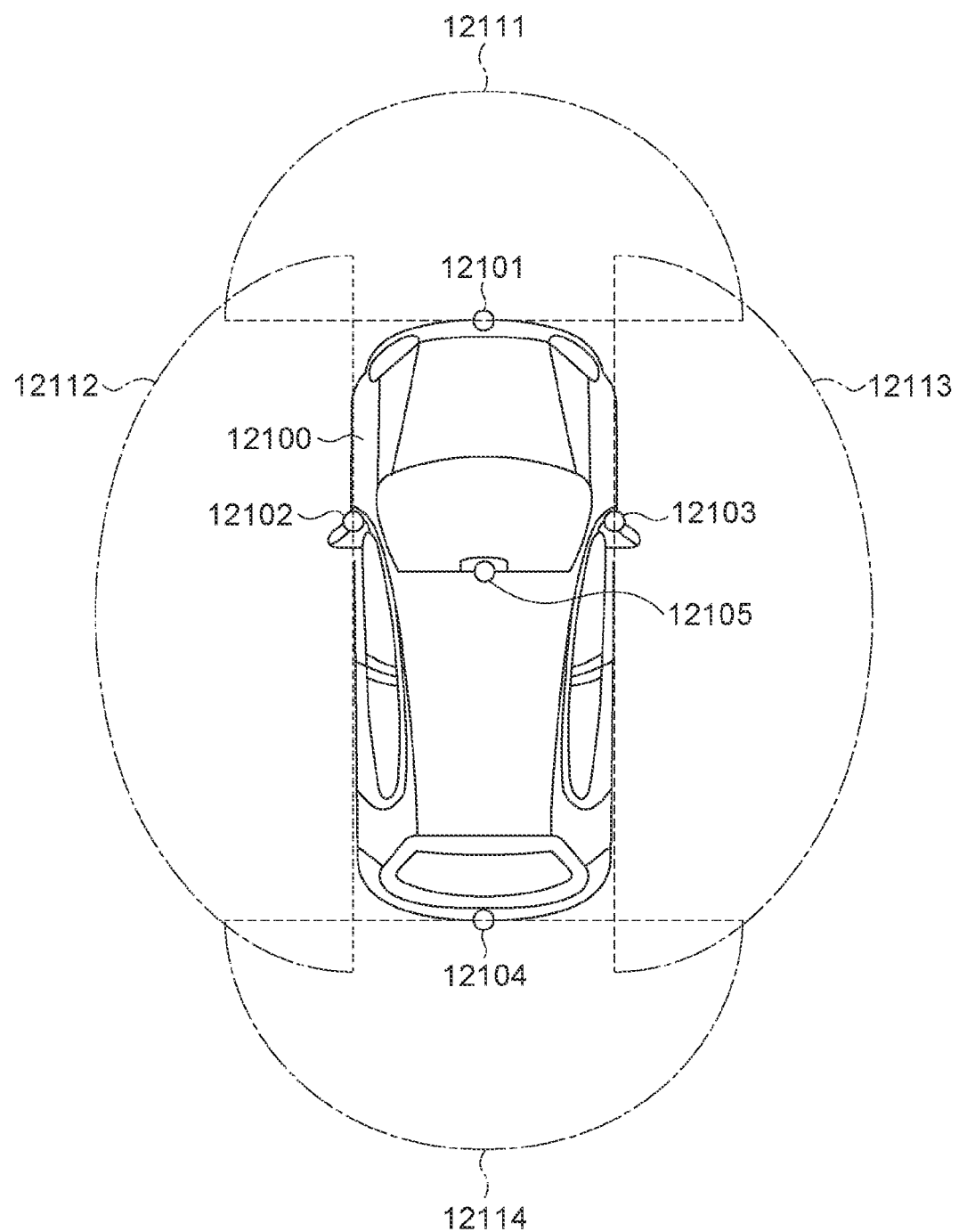
FIG. 28 is an explanatory diagram showing an example of installation positions of external information detectors and imagers.

FIG. 28 is a diagram showing an example of installation positions of imagers 12031.

In FIG. 28, a vehicle 12100 includes imagers 12101, 12102, 12103, 12104, and 12105 as the imagers 12031.

Imagers 12101, 12102, 12103, 12104, and 12105 are provided at the following positions: the front end edge of a vehicle 12100, a side mirror, the rear bumper, a rear door, an upper portion of the front windshield inside the vehicle, and the like, for example. The imager 12101 provided on the front end edge and the imager 12105 provided on the upper portion of the front windshield inside the vehicle mainly capture images ahead of the vehicle 12100. The imagers 12102 and 12103 provided on the side mirrors mainly capture images on the sides of the vehicle 12100. The imager 12104 provided on the rear bumper or a rear door mainly captures images behind the vehicle 12100. The front images acquired by the imagers 12101 and 12105 are mainly used for detection of a vehicle running in front of the vehicle 12100, a pedestrian, an obstacle, a traffic signal, a traffic sign, a lane, or the like.

Note that FIG. 28 shows an example of the imaging ranges of the imagers 12101 to 12104. An imaging range 12111 indicates the imaging range of the imager 12101 provided on the front end edge, imaging ranges 12112 and 12113 indicate the imaging ranges of the imagers 12102 and 12103 provided on the respective side mirrors, and an imaging range 12114 indicates the imaging range of the imager 12104 provided on the rear bumper or a rear door. For example, image data captured by the imagers 12101 to 12104 are superimposed on one another, so that an overhead image of the vehicle 12100 viewed from above is obtained.

At least one of the imagers 12101 to 12104 may have a function of acquiring distance information. For example, at least one of the imagers 12101 to 12104 may be a stereo camera including a plurality of imaging elements, or may be imaging elements having pixels for phase difference detection.

For example, on the basis of distance information obtained from the imagers 12101 to 12104, the microcomputer 12051 calculates the distances to the respective three-dimensional objects within the imaging ranges 12111 to 12114, and temporal changes in the distances (the velocities relative to the vehicle 12100). In this manner, the three-dimensional object that is the closest three-dimensional object on the traveling path of the vehicle 12100 and is traveling at a predetermined velocity (0 km/h or higher, for example) in substantially the same direction as the vehicle 12100 can be extracted as the vehicle running in front of the vehicle 12100. Further, the microcomputer 12051 can set beforehand an inter-vehicle distance to be maintained in front of the vehicle running in front of the vehicle 12100, and can perform automatic brake control (including follow-up stop control), automatic acceleration control (including follow-up start control), and the like. In this manner, it is possible to perform cooperative control to conduct automatic driving or the like to autonomously travel not depending on the operation of the driver.

For example, in accordance with the distance information obtained from the imagers 12101 to 12104, the microcomputer 12051 can extract three-dimensional object data concerning three-dimensional objects under the categories of two-wheeled vehicles, regular vehicles, large vehicles, pedestrians, utility poles, and the like, and use the three-dimensional object data in automatically avoiding obstacles. For example, the microcomputer 12051 classifies the obstacles in the vicinity of the vehicle 12100 into obstacles visible to the driver of the vehicle 12100 and obstacles difficult to visually recognize. The microcomputer 12051 then determines collision risks indicating the risks of collision with the respective obstacles. If a collision risk is equal to or higher than a set value, and there is a possibility of collision, the microcomputer 12051 can output a warning to the driver via the audio speaker 12061 and the display unit 12062, or can perform driving support for avoiding collision by performing forced deceleration or avoiding steering via the drive system control unit 12010.

At least one of the imagers 12101 to 12104 may be an infrared camera that detects infrared rays. For example, the microcomputer 12051 can recognize a pedestrian by determining whether or not a pedestrian exists in images captured by the imagers 12101 to 12104. Such pedestrian recognition is carried out through a process of extracting feature points from the images captured by the imagers 12101 to 12104 serving as infrared cameras, and a process of performing a pattern matching on the series of feature points indicating the outlines of objects and determining whether or not there is a pedestrian, for example. If the microcomputer 12051 determines that a pedestrian exists in the images captured by the imagers 12101 to 12104, and recognizes a pedestrian, the sound/image output unit 12052 controls the display unit 12062 to display a rectangular contour line for emphasizing the recognized pedestrian in a superimposed manner. Further, the sound/image output unit 12052 may also control the display unit 12062 to display an icon or the like indicating the pedestrian at a desired position.

An example of a vehicle control system to which the technology (the present technology) according to the present disclosure may be applied has been described above. The technology according to the present disclosure may be applied to the imager 12031 and the like among the components described above, for example. Specifically, the solid-state imaging device 111 of the present disclosure can be applied to the imager 12031. By applying the technique according to the present disclosure to the imager 12031, it is possible to improve the yield and reduce the manufacturing costs.

Note that the present technology is not limited to the embodiments and example applications described above, and various modifications may be made to them without departing from the scope of the present technology.

Further, the advantageous effects described in this specification are merely examples, and the advantageous effects of the present technology are not limited to them and may include other effects.

The present technology may also be embodied in the configurations described below.

[1]

An imaging device including a stereo imager, in which the stereo imager includes a plurality of sensors, each sensor of the plurality of sensors has an imaging unit formed with a plurality of repeating units, the imaging unit includes a polarizer having at least one kind of polarization spindle angle, and at least two unit images obtained by a plurality of the imaging units are combined, to obtain information about polarization in at least three directions, and generate normal information.

[2]

The imaging device according to [1], in which a polarizer having the at least one kind of polarization spindle angle included in one imaging unit of the plurality of imaging units, and a polarizer having the at least one kind of polarization spindle angle included in each of the plurality of imaging units other than the one imaging unit differ from each other in the polarization spindle angle, and each of the imaging units other than the one imaging unit does not include the polarizer having the at least one kind of polarization spindle angle included in the one imaging unit.

[3]

The imaging device according to [1] or [2], in which a plurality of the unit images is reconstructed on the basis of a stereo correspondence relationship.

[4]

The imaging device according to any one of [1] to [3], in which each imaging unit of the plurality of imaging units includes a polarizer having two or less kinds of the polarization spindle angles.

[5]

The imaging device according to any one of [1] to [4], in which each imaging unit of the plurality of imaging units includes a polarizer having two kinds of the polarization spindle angles, and the two kinds of the polarization spindle angles are orthogonal to each other in each imaging unit of the plurality of imaging units.

[6]

The imaging device according to any one of [1] to [5], in which one imaging unit of the plurality of imaging units includes a polarizer having a polarization spindle angle of 22.5 degrees and a polarizer having a polarization spindle angle of 112.5 degrees, and another imaging unit of the plurality of imaging units includes a polarizer having a polarization spindle angle of 67.5 degrees and a polarizer having a polarization spindle angle of 157.5 degrees.

[7]

The imaging device according to any one of [1] to [3], in which each imaging unit of the plurality of imaging units includes a polarizer having one kind of polarization spindle angle, and the difference in the polarization spindle angle among the polarizers of the respective imaging units of the plurality of imaging units is not smaller than five degrees and not greater than 85 degrees.

[8]

The imaging device according to any one of [1] to [7], in which each imaging unit of the plurality of imaging units has repeating units including a polarizer and repeating units not including a polarizer, and the ratio between the repeating units including a polarizer and the repeating units not including a polarizer is substantially the same among the respective imaging units of the plurality of imaging units.

[9]

The imaging device according to any one of [1] to [8], in which each imaging unit of the plurality of imaging units has repeating units including a polarizer and repeating units not including a polarizer, and the layout pattern of the repeating units including a polarizer and the repeating units not including a polarizer is substantially the same among the imaging units of the plurality of imaging units.

[10]

An imaging device including a stereo imager, in which the stereo imager includes a first sensor and a second sensor, the first sensor has a first imaging unit formed with a plurality of repeating units, the second sensor has a second imaging unit formed with a plurality of repeating units, the first imaging unit includes a polarizer having at least one kind of polarization spindle angle, the second imaging unit includes a polarizer having at least one kind of polarization spindle angle, a first unit image obtained by the first imaging unit and a second unit image obtained by the second imaging unit are combined, to acquire information about polarization in at least three directions, and generate normal information.

[11]

The imaging device according to [10], in which the polarizer of the first imaging unit having at least one kind of polarization spindle angle, and the polarizer of the second imaging unit having at least one kind of polarization spindle angle differ from each other in the polarization spindle angle, and the second imaging unit does not include the polarizer of the first imaging unit having at least one kind of polarization spindle angle.

[12]

The imaging device according to [10] or [11], in which the first unit image and the second unit image are reconstructed on the basis of a stereo correspondence relationship.

[13]

The imaging device according to any one of [10] to [12], in which the first imaging unit includes a polarizer having two or less kinds of polarization spindle angles, and the second imaging unit includes a polarizer having two or less kinds of polarization spindle angles.

[14]

The imaging device according to any one of [10] to [13], in which the first imaging unit includes a polarizer having two kinds of polarization spindle angles, and the two kinds of polarization spindle angles are orthogonal to each other in the first imaging unit, and the second imaging unit includes a polarizer having two kinds of polarization spindle angles, and the two kinds of polarization spindle angles are orthogonal to each other in the second imaging unit.

[15]

The imaging device according to any one of [10] to [14], in which the first imaging unit includes a polarizer having a polarization spindle angle of 22.5 degrees and a polarizer having a polarization spindle angle of 112.5 degrees, and the second imaging unit includes a polarizer having a polarization spindle angle of 67.5 degrees and a polarizer having a polarization spindle angle of 157.5 degrees.

[16]

The imaging device according to any one of [10] to [12], in which the first imaging unit includes a polarizer having one kind of polarization spindle angle, the second imaging unit includes a polarizer having one kind of polarization spindle angle, and a difference between the polarization spindle angle of the polarizer included in the first imaging unit and the polarization spindle angle of the polarizer included in the second imaging unit is not smaller than five degrees and not greater than 85 degrees.

[17]

The imaging device according to any one of [10] to [16], in which the first imaging unit has repeating units including a polarizer and repeating units not including a polarizer, the second imaging unit has repeating units including a polarizer and repeating units not including a polarizer, and a ratio between the repeating units including a polarizer and the repeating units not including a polarizer in the first imaging unit, and a ratio between the repeating units including a polarizer and the repeating units not including a polarizer in the second imaging unit are substantially the same.

[18]

The imaging device according to any one of [10] to [17], in which the first imaging unit has repeating units including a polarizer and repeating units not including a polarizer, the second imaging unit has repeating units including a polarizer and repeating units not including a polarizer, and a layout pattern of the repeating units including a polarizer and the repeating units not including a polarizer in the first imaging unit, and a layout pattern the repeating units including a polarizer and the repeating units not including a polarizer in the second imaging unit are substantially the same.

[19]

An electronic apparatus including the imaging device according to any one of [1] to [18].

REFERENCE SIGNS LIST 1, 2, 3, 4, 5, 6, 7, 8, 9, 10A, 11, 12, 13, 14, 15 Imaging device
1-1, 1-2, 2-1, 2-2, 3-1, 3-2, 4-1, 4-2, 5-1, 5-2, 6-1, 6-2, 7-1, 7-2, 8-1, 8-2, 9-1, 9-2, 10A-1, 10A-2, 10A-3, 11-1, 11-2, 12-1, 12-2, 13-1, 13-2, 14-1, 14-2, 15-1, 15-2, 16-1, 17-1 Sensor 10(10-1, 10-2), 20(20-1, 20-2), 30(30-1, 30-2), 40(40-1, 40-2), 50(50-1, 50-2), 60(60-1, 60-2), 70(70-1, 70-2), 80(80-1, 80-2), 90(90-1, 90-2), 100(100-1, 100-2), 110(110-1-1, 110-1-2, 110-2-1, 110-2-2), 120(120-1-1, 120-1-2, 120-2-1, 120-2-2), 130(130-1R, 130-1G, 130-1B, 130-2R, 130-2G, 130-2B), 140(140-1, 140-2), 150 (150-1R, 150-1G, 150-1B, 150-2R, 150-2G, 150-2B) Imaging unit (unit image)
167(167-1, 167-2), 177(177-1, 177-2) Polarizer

The invention claimed is:

1. An imaging device, comprising:
a stereo imager, wherein
the stereo imager includes a plurality of sensors that corresponds to a plurality of imaging units,
each sensor of the plurality of sensors has an imaging unit of the plurality of imaging units, wherein the imaging unit has a plurality of repeating units,
each imaging unit of the plurality of imaging units includes a polarizer having at least one kind of polarization spindle angle,
a difference in the polarization spindle angle among polarizers of the respective imaging units of the plurality of imaging units is not smaller than five degrees and not greater than 85 degrees, and
the plurality of imaging units is configured to:
generate at least two unit images; and
obtain information about polarization in at least three directions and to generate normal information based on a combination of the at least two unit images.

2. The imaging device according to claim 1, wherein the at least two unit images are reconstructed based on a stereo correspondence relationship.

3. The imaging device according to claim 1, wherein the polarizer of each imaging unit of the plurality of imaging units has two or less kinds of polarization spindle angles.

4. The imaging device according to claim 1, wherein
each imaging unit of the plurality of imaging units includes the polarizer having two kinds of polarization spindle angles, and
the two kinds of the polarization spindle angles are orthogonal to each other.

5. The imaging device according to claim 1, wherein
a first imaging unit of the plurality of imaging units includes a first polarizer having a first polarization spindle angle of 22.5 degrees and a second polarizer having a second polarization spindle angle of 112.5 degrees, and
a second imaging unit of the plurality of imaging units includes a third polarizer having a third polarization spindle angle of 67.5 degrees and a fourth polarizer having a fourth polarization spindle angle of 157.5 degrees.

6. The imaging device according to claim 1, wherein
each imaging unit of the plurality of imaging units has a first set of repeating units of the plurality of repeating units that includes the polarizer and a second set of repeating units of the plurality of repeating units that does not include the polarizer, and
a ratio between the first set of repeating units and the second set of repeating units is substantially the same among the respective imaging units of the plurality of imaging units.

7. The imaging device according to claim 1, wherein
each imaging unit of the plurality of imaging units has a first set of repeating units of the plurality of repeating units that includes the polarizer and a second set of repeating units of the plurality of repeating units that does not include the polarizer, and
a layout pattern of the first set of repeating units and the second set of repeating units is substantially the same among the respective imaging units of the plurality of imaging units.

8. An imaging device, comprising
a stereo imager, wherein
the stereo imager includes a first sensor and a second sensor,
the first sensor has a first imaging unit, wherein the first imaging unit has a plurality of first repeating units,
the second sensor has a second imaging unit, wherein the second imaging unit has a plurality of second repeating units,
the first imaging unit includes a first polarizer having at least one kind of first polarization spindle angle,
the second imaging unit includes a second polarizer having at least one kind of second polarization spindle angle, and
a difference between the first polarization spindle angle of the first polarizer in the first imaging unit and the second polarization spindle angle of the second polarizer in the second imaging unit is not smaller than five degrees and not greater than 85 degrees
the first imaging unit is configured to generate a first unit image;
the second imaging unit is configured to generate a second unit image; and
the first imaging unit and the second imaging unit are configured to obtain information about polarization in at least three directions and generate normal information based on a combination of the first unit image and the second unit image.

9. The imaging device according to claim 8, wherein
the first polarization spindle angle is different from the second polarization spindle angle, and
the first polarizer is different from the second polarizer.

10. The imaging device according to claim 8, wherein the first unit image and the second unit image are reconstructed based on a stereo correspondence relationship.

11. The imaging device according to claim 8, wherein
the polarizer of the first imaging unit has two or less kinds of polarization spindle angles, and
the polarizer of the second imaging unit has two or less kinds of polarization spindle angles.

12. The imaging device according to claim 8, wherein
the polarizer of the first imaging unit has two kinds of polarization spindle angles, and the two kinds of polarization spindle angles are orthogonal to each other, and the polarizer of the second imaging unit has two kinds of polarization spindle angles, and the two kinds of polarization spindle angles are orthogonal to each other.

13. The imaging device according to claim 8, wherein
the first imaging unit includes the first polarizer having the first polarization spindle angle of 22.5 degrees and a third polarizer having a third polarization spindle angle of 112.5 degrees, and
the second imaging unit includes the second polarizer having the second polarization spindle angle of 67.5 degrees and a fourth polarizer having a fourth polarization spindle angle of 157.5 degrees.

14. The imaging device according to claim 8, wherein
the first imaging unit has a first set of the plurality of first repeating units that includes the first including a polarizer and a second set of the plurality of first repeating units that does not include the first polarizer,
the second imaging unit has a third set of the plurality of second repeating units that includes the second polarizer and a fourth set of the plurality of second repeating units that does not include the second polarizer, and
a ratio between the first set of the plurality of first repeating units and the second set of the plurality of first repeating units in the first imaging unit, and a ratio between the third set of the plurality of second repeating units and the fourth set of the plurality of second repeating units in the second imaging unit are substantially the same.

15. The imaging device according to claim 8, wherein
the first imaging unit has a first set of the plurality of first repeating units that includes the first polarizer and a second set of the plurality of first repeating units that does not include the first polarizer,
the second imaging unit has a third set of the plurality of second repeating units that includes the second polarizer and a fourth set of the plurality of second repeating units that does not include the second polarizer, and
a layout pattern of the first set of the plurality of first repeating units and the second set of the plurality of first repeating units in the first imaging unit, and a layout pattern of the third set of the plurality of second repeating units and the fourth set of the plurality of second repeating units in the second imaging unit are substantially the same.

16. An electronic apparatus, comprising:
an imaging device that comprises:
a stereo imager, wherein
the stereo imager includes a plurality of sensors that corresponds to a plurality of imaging units,
each sensor of the plurality of sensors has an imaging unit of the plurality of imaging units, wherein the imaging unit has a plurality of repeating units,
each imaging unit of the plurality of imaging units includes a polarizer having at least one kind of polarization spindle angle,
a difference in the polarization spindle angle among polarizers of the respective imaging units of the plurality of imaging units is not smaller than five degrees and not greater than 85 degrees, and
the plurality of imaging units is configured to:
generate at least two unit images; and
obtain information about polarization in at least three directions and to generate normal information based on a combination of the at least two unit images.

17. An electronic apparatus, comprising:
an imaging device that comprises:

a stereo imager, wherein
- the stereo imager includes a first sensor and a second sensor,
- the first sensor has a first imaging unit, wherein the first imaging unit has a plurality of first repeating units,
- the second sensor has a second imaging unit, wherein the second imaging unit has a plurality of second repeating units,
- the first imaging unit includes a first polarizer having at least one kind of first polarization spindle angle,
- the second imaging unit includes a second polarizer having at least one kind of second polarization spindle angle, and
- a difference between the first polarization spindle angle of the first polarizer in the first imaging unit and the second polarization spindle angle of the second polarizer in the second imaging unit is not smaller than five degrees and not greater than 85 degrees the first imaging unit is configured to generate a first unit image;

the second imaging unit is configured to generate a second unit image; and the first imaging unit and the second imaging unit is configured to obtain information about polarization in at least three directions, and to generate normal information based on a combination of the first unit image and the second unit image.

* * * * *